United States Patent
Lee et al.

(10) Patent No.: US 10,806,433 B2
(45) Date of Patent: Oct. 20, 2020

(54) ULTRASOUND APPARATUS AND METHOD OF OPERATING THE SAME

(71) Applicant: SAMSUNG MEDISON CO., LTD., Hongcheon-gun (KR)

(72) Inventors: Yong-il Lee, Hongcheon-gun (KR); Hyoung-jin Kim, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 1309 days.

(21) Appl. No.: 15/003,964

(22) Filed: Jan. 22, 2016

(65) Prior Publication Data
US 2016/0220231 A1     Aug. 4, 2016

(30) Foreign Application Priority Data

Jan. 29, 2015 (KR) .................... 10-2015-0014590

(51) Int. Cl.
*A61B 8/00* (2006.01)
*A61B 8/06* (2006.01)
(Continued)

(52) U.S. Cl.
CPC ................ *A61B 8/469* (2013.01); *A61B 8/04* (2013.01); *A61B 8/06* (2013.01); *A61B 8/463* (2013.01);
(Continued)

(58) Field of Classification Search
CPC .. A61B 8/469; A61B 8/04; A61B 8/06; A61B 8/463
See application file for complete search history.

(56) References Cited

U.S. PATENT DOCUMENTS 5,365,929 A   11/1994  Peterson
5,383,463 A    1/1995  Friedman
(Continued)

FOREIGN PATENT DOCUMENTS

JP   10-165400 A    6/1998
JP    5054361 B2   10/2012
(Continued)

OTHER PUBLICATIONS

"Ultrasound", Neuroradiology, https://sites.google.com/a/wisc.edu/neuroradioloay/image-acquisition/vasoular-imaging/ultrasound, 2011.
(Continued)

*Primary Examiner* — Joseph M Santos Rodriguez
(74) *Attorney, Agent, or Firm* — Sughrue Mion, PLLC

(57) ABSTRACT

An ultrasound apparatus includes: a data obtaining unit configured to obtain ultrasound data of an object; a controller configured to generate an ultrasound image based on the ultrasound data, obtain blood flow information of the object by using a Doppler component obtained from the ultrasound data, and set a plurality of sample volume gates based on the blood flow information; and a display configured to display the ultrasound image in which the plurality of sample volume gates are displayed. The ultrasound apparatus may reduce a processing time of the ultrasound apparatuses and simplify a user's manipulation by obtaining an ultrasound image one time and providing a plurality of Doppler spectrums.

28 Claims, 22 Drawing Sheets

(51) Int. Cl.
*A61B 8/08* (2006.01)
*A61B 8/04* (2006.01)
*G01S 7/52* (2006.01)
*G01S 15/89* (2006.01)

(52) U.S. Cl.
CPC .............. *A61B 8/483* (2013.01); *A61B 8/488* (2013.01); *A61B 8/5207* (2013.01); *A61B 8/5223* (2013.01); *A61B 8/54* (2013.01); *A61B 8/0891* (2013.01); *A61B 8/4405* (2013.01); *A61B 8/4427* (2013.01); *A61B 8/565* (2013.01); *G01S 7/52074* (2013.01); *G01S 7/52084* (2013.01); *G01S 15/8979* (2013.01)

(56) References Cited

U.S. PATENT DOCUMENTS

| | | | |
|---|---|---|---|
| 6,423,006 | B1 | 7/2002 | Banjanin |
| 6,450,959 | B1 | 9/2002 | Mo et al. |
| 7,798,964 | B2 | 9/2010 | Kim et al. |
| 8,036,856 | B2 | 10/2011 | Pan et al. |
| 2005/0075568 | A1* | 4/2005 | Moehring ................ A61B 8/06 600/453 |
| 2010/0022884 | A1 | 1/2010 | Ustuner et al. |
| 2010/0286523 | A1 | 11/2010 | Kim et al. |
| 2013/0184578 | A1 | 7/2013 | Lee et al. |
| 2013/0281855 | A1* | 10/2013 | Baba ........................ A61B 8/06 600/441 |
| 2014/0018680 | A1* | 1/2014 | Guracar ................. A61B 8/463 600/440 |
| 2014/0276057 | A1 | 9/2014 | Lee et al. |
| 2014/0303499 | A1 | 10/2014 | Toma et al. |

FOREIGN PATENT DOCUMENTS

| | | |
|---|---|---|
| JP | 2014-68980 A | 4/2014 |
| KR | 2001-0016995 A | 3/2001 |

OTHER PUBLICATIONS

"Associations of Carotid Artery Intima-Media Thickness (IMT) With Risk Factors and Prevalent Cardiovascular Disease", http://www.jultrasoundmed.org/content/29/12/1759/F1.expansion, Dec. 1, 2010, vol. 29, No. 12.

A. Granata; et al; "Doppler ultrasound and renal artery stenosis: An Overview"; J. Ultrasound; Dec. 2009; vol. 12; No. 4; pp. 133-143.

Communication dated Jun. 28, 2016 issued by European Patent Office in counterpart European Application No. 16150291.9.

* cited by examiner

ULTRASOUND APPARATUS AND METHOD OF OPERATING THE SAME

CROSS-REFERENCE TO RELATED APPLICATION

This application claims the benefit of Korean Patent Application No. 10-2015-0014590, filed on Jan. 29, 2015, in the Korean Intellectual Property Office, the disclosure of which is incorporated herein in its entirety by reference.

BACKGROUND

1. Field

The present disclosure relates to ultrasound apparatuses and methods of operating the same, and more particularly, to ultrasound apparatuses for setting a sample volume gate in order to perform Doppler diagnosis, and methods of operating the same.

2. Description of the Related Art

Ultrasound diagnosis apparatuses transmit ultrasound signals generated by transducers of a probe to an object and receive echo signals reflected from the object, thereby obtaining at least one image of an internal part of the object (e.g., soft tissues or blood flow). In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure, compared to X-ray apparatuses. Therefore, ultrasound diagnosis apparatuses are widely used together with other image diagnosis apparatuses including a computed tomography (CT) apparatus, a magnetic resonance imaging (MRI) apparatus, and the like.

SUMMARY

Exemplary embodiments may reduce a processing time of ultrasound apparatuses and simplify a user's manipulation by obtaining an ultrasound image one time and providing a plurality of Doppler spectrums.

Additional aspects will be set forth in part in the description which follows and, in part, will be apparent from the description, or may be learned by practice of the presented exemplary embodiments.

According to an aspect of an exemplary embodiment, an ultrasound apparatus includes: a data obtaining unit configured to obtain ultrasound data of an object; a controller configured to generate an ultrasound image based on the ultrasound data, obtain blood flow information of the object by using a Doppler component obtained from the ultrasound data, and set a plurality of sample volume gates based on the blood flow information; and a display configured to display the ultrasound image in which the plurality of sample volume gates are displayed.

The apparatus may further include: a user interface configured to receive a user input for setting at least one sample volume gate from among the plurality of sample volume gates at a predetermined location of the object displayed on the ultrasound image, wherein the controller may set the at least one sample volume gate based on the user input.

The user input may include at least one of an input for setting an interested region on the ultrasound image and an input for setting an interested location of the at least one sample volume gate in the interested region.

The input for setting the interested location may include at least one of an input for moving the interested location to at least one scan line displayed on the ultrasound image, an input for setting a scan depth of the at least one scan line in response to the interested location, and an input for setting an angle of a sample volume gate that corresponds to a stream line corresponding to blood flow of the object.

The controller may obtain the blood flow information by using vector information representing blood flow velocity and direction of the object.

The blood flow information may include at least one of the blood flow velocity, a blood flow amount, a blood flow pressure, and a blood flow angle.

The controller may estimate a stream line corresponding to the blood flow by using the vector information, and set a point having a maximum magnitude of a blood flow velocity on the stream line to a first candidate sample volume gate.

The controller may set a point having a minimum magnitude of a blood flow velocity inside the interested region of the ultrasound image to a second candidate sample volume gate based on the stream line and the first candidate sample volume gate.

The controller may set points separated by a predetermined distance according to a number of required sample volume gates to a plurality of candidate sample volume gates based on the stream line and the first candidate sample volume gate.

The display may display the ultrasound image in which the first candidate sample volume gate and the second candidate sample volume gate are displayed.

The apparatus may further include: a user interface configured to receive a user input that determines at least one of the first candidate sample volume gate and the second candidate sample volume gate as the at least one sample volume gate.

The user interface may receive a user input for adjusting at least one of the first candidate sample volume gate and the second candidate sample volume gate.

The object may include the carotid or the renal artery.

The controller may set a first sample volume gate at a predetermined location of the carotid on the ultrasound image in response to a maximum constriction point from among a constriction portion of the carotid.

The display may display a plurality of Doppler spectrums respectively corresponding to the plurality of sample volume gates.

The plurality of Doppler spectrums may have the same time information.

The user interface may receive an input for selecting a first sample volume gate from among the plurality of sample volume gates, and the display may display a first Doppler spectrum corresponding to the first sample volume gate.

According to an aspect of another exemplary embodiment, an ultrasound apparatus includes: a display configured to display an ultrasound image obtained from ultrasound data of an object; a user interface configured to receive a user input for setting at least one of a plurality of sample volume gates corresponding to an interested location of the object at a predetermined location of the object displayed on the ultrasound image; and a controller configured to set the at least one sample volume gate based on the user input.

According to an aspect of another exemplary embodiment, a method of operating an ultrasound apparatus includes: obtaining ultrasound data of an object, and generating an ultrasound image based on the ultrasound data; obtaining blood flow information of the object by using a Doppler component obtained from the ultrasound data;

setting a plurality of sample volume gates based on the blood flow information; and displaying the ultrasound image in which the plurality of sample volume gates are displayed.

The method may further include: receiving a user input for setting at least one sample volume gate from among the plurality of sample volume gates at a predetermined location of the object displayed on the ultrasound image, wherein the setting of the plurality of sample volume gates may include: setting the at least one sample volume gate based on the user input.

The receiving of the user input may include: receiving at least one of an input for setting an interested region on the ultrasound image and an input for setting an interested location of the at least one sample volume gate in the interested region.

The receiving of the user input may include: receiving at least one of an input for moving the interested location to at least one scan line displayed on the ultrasound image, an input for setting a scan depth of the at least one scan line in response to the interested location, and an input for setting an angle of at least one sample volume gate that corresponds to a stream line corresponding to blood flow of the object.

The obtaining of the blood flow information of the object may include: obtaining the blood flow information by using vector information representing blood flow velocity and direction of the object.

The setting of the plurality of sample volume gates may include: estimating a stream line corresponding to the blood flow by using the vector information, and setting a point having a maximum magnitude of a blood flow velocity on the stream line to a first candidate sample volume gate.

The setting of the plurality of sample volume gates may include: setting a point having a minimum magnitude of a blood flow velocity or a point separated by a predetermined distance from the first candidate sample volume gate inside the interested region of the ultrasound image to a second candidate sample volume gate based on the stream line and the first candidate sample volume gate.

The method may further include: displaying the ultrasound image in which the first candidate sample volume gate and the second candidate sample volume gate are displayed.

The method may further include: receiving a user input that determines at least one of the first candidate sample volume gate and the second candidate sample volume gate as at least one sample volume gate of the plurality of sample volume gates.

The method may further include: receiving a user input for adjusting at least one of the first candidate sample volume gate and the second candidate sample volume gate.

According to an aspect of another exemplary embodiment, a method of operating an ultrasound apparatus includes: displaying an ultrasound image obtained from ultrasound data of an object; receiving a user input for setting at least one of a plurality of sample volume gates corresponding to an interested location of the object at a predetermined location of the object displayed on the ultrasound image; and setting the at least one sample volume gate based on the user input.

BRIEF DESCRIPTION OF THE DRAWINGS

Embodiments of the invention now will be described more fully hereinafter with reference to the accompanying drawings, in which reference numerals denote structural elements.

DETAILED DESCRIPTION

Figure 1:
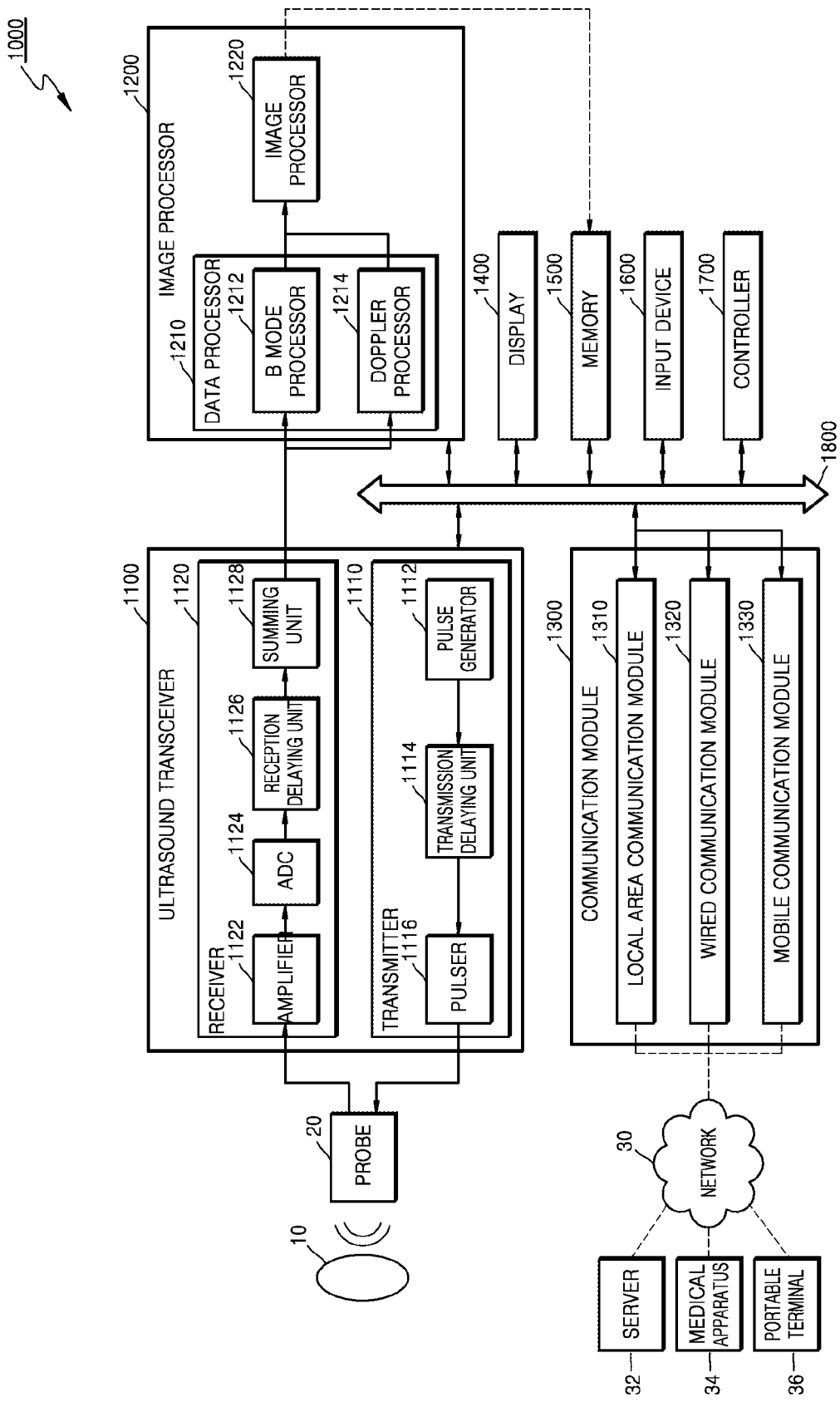
FIG. 1 is a block diagram illustrating a configuration of an ultrasound diagnosis apparatus according to an exemplary embodiment.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

When a part "includes" or "comprises" an element, unless there is a particular description contrary thereto, the part can further include other elements, not excluding the other elements. In addition, terms such as " . . . unit", " . . . module", or the like refer to units that perform at least one function or operation, and the units may be implemented as hardware or software or as a combination of hardware and software. Also, the term "unit" in the embodiments of the present disclosure means a software component or hardware components such as a field-programmable gate array (FPGA) or an application-specific integrated circuit (ASIC), and performs a specific function.

However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables.

A function provided by the components and "units" may be associated with the smaller number of components and "units", or may be divided into additional components and "units".

While such terms as "first," "second," etc., may be used to describe various components, such components must not be limited to the above terms. The above terms are used only to distinguish one component from another. For example, a first component may be referred to as a second component without departing from the scope of the inventive concept, and similarly, the second component may be referred to as the first component. A term "and/or" includes a combination of a plurality of related described items or includes one of a plurality of related described items.

Throughout the specification, an "image" may denote multi-dimensional data including discrete image elements (for example, pixels in a two-dimensional (2D) image, and voxels in a three-dimensional (3D) image).

Throughout the specification, an "ultrasound image" refers to an image of an object, which is obtained using ultrasound waves. An ultrasound image may denote an image obtained by irradiating an ultrasound signal generated from a transducer of a probe to an object and receiving information of an echo signal reflected by the object. Also, an ultrasound image may be implemented variously, and for example, the ultrasound image may be at least one of an amplitude (A) mode image, a brightness (B) mode image, a color (C) mode image, and a Doppler (D) mode image, and also the ultrasound image may be a 2D image or a 3D image.

Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Furthermore, throughout the specification, a "user" may be, but is not limited to, a medical expert, such as a medical doctor, a nurse, a medical laboratory technologist, a medical image expert, or a technician who repairs a medical apparatus.

Hereinafter, exemplary embodiments will be described in detail with reference to the accompanying drawings.

Reference will now be made in detail to embodiments, examples of which are illustrated in the accompanying drawings. In this regard, the present embodiments may have different forms and should not be construed as being limited to the descriptions set forth herein.

FIG. 1 is a block diagram showing a configuration of an ultrasound diagnosis apparatus 1000 according to an embodiment.

Referring to FIG. 1, the ultrasound diagnosis apparatus 1000 may include a probe 20, an ultrasound transceiver 1100, an image processor 1200, a communication module 1300, a display 1400, a memory 1500, an input device 1600, and a controller 1700, which may be connected to one another via buses 1800. A person of ordinary skill in the art will understand that other general components may be further included besides the components illustrated in FIG. 1.

The ultrasound diagnosis apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly, and according to embodiments, the ultrasound diagnosis apparatus 1000 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 1124 by delay times necessary for determining reception directionality, and the summing unit 1128 generates ultrasound data by summing the echo signals processed by the reception delaying unit 1126. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 extracts B mode components from ultrasound data and processes the B mode components. An image generator 1220 may generate an ultrasound image indicating signal intensities as brightness based on the extracted B mode components 1212.

Similarly, a Doppler processor 1214 may extract Doppler components from ultrasound data, and the image generator 1220 may generate a Doppler image indicating a movement of an object as colors or waveforms based on the extracted Doppler components.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound diagnosis apparatus 1000 on a screen image via a graphical user interface (GUI). In addition, the ultrasound diagnosis apparatus 1000 may include two or more displays 1400 according to embodiments.

The display 1400 may include at least one of a liquid crystal display, a thin film transistor-liquid crystal display, an organic light-emitting diode, a flexible display, a 3D display, and an electrophoretic display.

Also, in the case where the display 1400 and a user input unit form a layer structure and configure a touchscreen, the display 1400 may be also used as an input unit that may receive information via a user's touch in addition to an output unit.

The touchscreen may be configured to detect not only a touch input location and a touched area but also a touch pressure. Also, the touchscreen may be configured to detect not only a real-touch but also a proximity touch.

In the present specification, a "real-touch" denotes a case where a pointer is actually touched on a screen, and a "proximity-touch" denotes a case where a pointer is not actually touched on a screen and approaches apart from the screen by a predetermined distance. In the present specification, a pointer denotes a touch tool for touching or proximity-touching a specific portion of a displayed screen. For example, a pointer may be an electronic pen, a finger, etc.

Though not shown, an ultrasound diagnosis apparatus 1000 may have various sensors inside or in the neighborhood of the touchscreen in order to detect a direct touch or a proximity touch for the touchscreen. An example of a sensor for detecting a touch of the touchscreen includes a tactile sensor.

The tactile sensor denotes a sensor that detects a contact of a specific object by using a degree or more felt by a user. The tactile sensor may detect various information such as roughness of a contact plane, rigidity of a contact object, temperature of a contact point, etc.

Also, an example of a sensor for detecting a touch of the touchscreen includes a proximity sensor. The proximity sensor denotes a sensor that detects existence of an object approaching a predetermined detection surface, or an object existing in the neighborhood by using electromagnetic force or an infrared ray without a mechanical contact.

Examples of the proximity sensor include a transmissive photo-electric sensor, a direct reflective photo-electric sensor, a mirror reflective photo-electric sensor, a high frequency oscillation type proximity sensor, a capacitive proximity sensor, a magnetic proximity sensor, an infrared proximity sensor, etc.

In this case, the ultrasound diagnosis apparatus 1000 according to an exemplary embodiment may display an ultrasound image of a predetermined mode and a control panel for the ultrasound image on the touchscreen. Also, the ultrasound diagnosis apparatus 1000 may detect a user's touch gesture for the ultrasound image via the touchscreen.

The ultrasound diagnosis apparatus 1000 according to an exemplary embodiment may physically have a portion of buttons frequently used by a user from among buttons included in a control panel of the general ultrasound apparatus, and provide the rest of the buttons in the form of a graphical user interface (GUI) via the touchscreen.

The communication module 1300 is connected to a network 30 by wire or wirelessly to communicate with an external device or a server. The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is connected to the network 30 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis apparatus 1000. For example, the memory 1500 may store medical data related to diagnosis of an object, such as ultrasound data and an ultrasound image that are input or output, and may also store algorithms or programs which are to be executed in the ultrasound diagnosis apparatus 1000.

The memory 1500 may be any of various storage media, e.g., a flash memory, a hard disk drive, EEPROM, etc. Furthermore, the ultrasound diagnosis apparatus 1000 may utilize web storage or a cloud server that performs the storage function of the memory 1500 online.

The input device 1600 refers to a means via which a user inputs data for controlling the ultrasound diagnosis apparatus 1000. The input device 1600 may include hardware components, such as a keypad, a mouse, a touch pad, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound diagnosis apparatus 1000. In other words, the controller 1700 may control operations among the probe 20, the ultrasound transceiver 1100, the image processor 1200, the communication module 1300, the display 1400, the memory 1500, and the input device 1600 shown in FIG. 1.

All or some of the probe 20, the ultrasound transceiver 1100, the image processor 1200, the communication module 1300, the display 1400, the memory 1500, the input device 1600, and the controller 1700 may be implemented as software modules. Also, at least one of the ultrasound transmission/reception unit 1100, the image processor 1200, and the communication module 1300 may be included in the control unit 1600; however, the inventive concept is not limited thereto.

Figure 2:
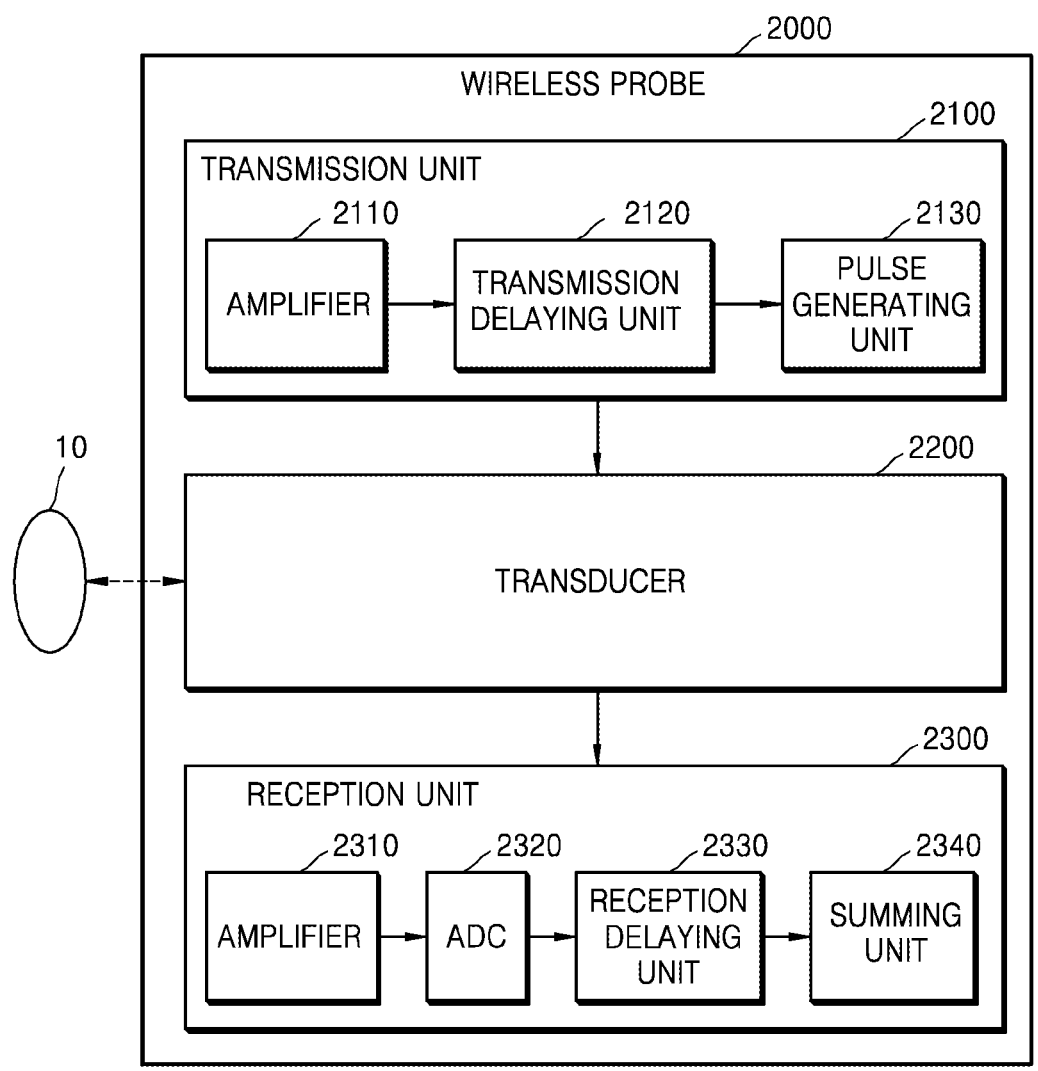
FIG. 2 is a block diagram illustrating a configuration of a wireless probe according to an exemplary embodiment.

FIG. 2 is a block diagram showing a configuration of a wireless probe 2000 according to an embodiment.

As described above with reference to FIG. 1, the wireless probe 2000 may include a plurality of transducers, and, according to embodiments, may include some or all of the components of the ultrasound transceiver 100 shown in FIG. 1.

The wireless probe 2000 according to the embodiment shown in FIG. 2 includes a transmitter 2100, a transducer 2200, and a receiver 2300. Since descriptions thereof are given above with reference to FIG. 1, detailed descriptions thereof will be omitted here. In addition, according to embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound diagnosis apparatus 1000 shown in FIG. 1.

The wireless probe 2000 may be a smart device that may perform ultrasound scanning by including a transducer array. Specifically, the wireless probe 2000 is a smart device and obtains ultrasound data by scanning an object by using the transducer array. Then, the wireless probe 2000 may generate and/or display an ultrasound image by using the obtained ultrasound data. The wireless probe 2000 may include a display, and display a screen including a user interface screen for controlling at least one ultrasound image and/or a scan operation of an object via the display.

While a user scans a predetermined body portion of a patient, which is an object, by using the wireless probe 2000, the wireless probe 2000 and the ultrasound diagnosis apparatus 1000 may continuously transmit/receive predetermined data via a wireless network. Specifically, while the user scans the predetermined body portion of the patient, which is an object, by using the wireless probe 2000, the wireless probe 2000 may transmit, in real-time, ultrasound data to the ultrasound diagnosis apparatus 1000 via the wireless network. While the ultrasound scanning is continuously performed, the ultrasound data may be updated in real-time and transmitted from the wireless probe 2000 to the ultrasound diagnosis apparatus 1000.

Figure 3A:
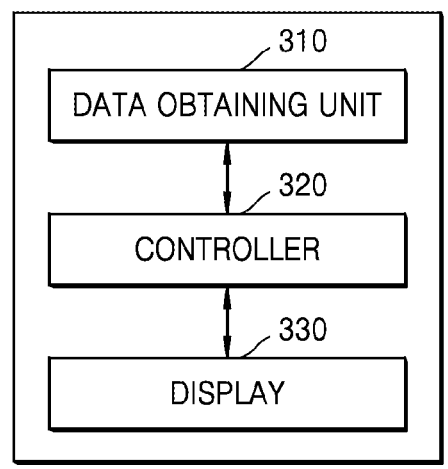
FIG. 3A is a block diagram illustrating a configuration of an ultrasound apparatus according to an exemplary embodiment.

FIG. 3A is a block diagram illustrating configuration of an ultrasound apparatus 300 according to an exemplary embodiment.

According to an exemplary embodiment, the ultrasound apparatus 300 may include a data obtaining unit 310, a controller 320, and a display 330. However, not all illustrated components are not essential components. The ultrasound apparatus 300 may be implemented by using a greater number of components than a number of illustrated components, and may be implemented by a smaller number of components.

Since the data obtaining unit 310, the controller 320, and the display 330 of the ultrasound apparatus 300 may equally correspond to the ultrasound transceiver 1100, the image processor 1200, and the display 1400 of the ultrasound diagnosis apparatus 100 illustrated in FIG. 1, and repeated descriptions of FIG. 1 are omitted.

The data obtaining unit 310 obtains ultrasound data of an object. For example, the ultrasound apparatus 300 may further include a probe. When a predetermined region of the object is scanned via the probe, the probe of the object obtains ultrasound data. The data obtaining unit 310 obtains ultrasound data via the probe. More specifically, the probe obtains ultrasound data corresponding to an ultrasound image by transmitting an ultrasound signal to the object, and receiving an ultrasound signal (that is, an ultrasound echo signal) reflected by the object.

Also, the data obtaining unit 310 may obtain ultrasound data via the probe, but may obtain ultrasound data from an external device physically independent of the ultrasound apparatus 300.

Here, the external device is a device for obtaining, storing, processing, or using data related to an ultrasound image, and may be a medical image device, a medical server, a mobile terminal, or all computing devices capable of using and processing a medical image. For example, the external device may be a medical diagnosis device included inside a medical organization such as a hospital. Also, the external device may be a server for recording and storing a diagnosis history of a patient included inside a hospital, a medical image device required when a doctor reads a medical image in a hospital, etc.

Here, the object may correspond to the carotid. The ultrasound apparatus 300 provides an ultrasound image obtained by using ultrasound data. A doctor may diagnose a patient's carotid artery stenosis via the ultrasound image. A flow degree of blood flow with respect to a measurement location of the carotid is used for diagnosing a carotid artery stenosis. The flow degree of blood flow may be detected based on an ultrasound image obtained by the ultrasound apparatus 300. A Doppler flow velocity may be a criterion in diagnosing a carotid artery stenosis. The ultrasound apparatus 300 may set a sample volume gate at a predetermined location of the carotid on the ultrasound image, and provide a Doppler spectrum for the sample volume gate. A blood flow velocity of the carotid may be obtained from the Doppler spectrum.

Also, an object may correspond to the renal artery. The ultrasound apparatus 300 provides an ultrasound image obtained by using ultrasound data. A doctor may diagnose a patient's renal artery stenosis via the ultrasound image. The ultrasound apparatus 300 may set a sample volume gate at a predetermined location of the renal artery on the ultrasound image, and provide a Doppler spectrum for the sample volume gate.

The controller 320 generates an ultrasound image based on ultrasound data. The controller 320 provides a B (brightness) mode image showing a reflection coefficient of an ultrasound signal (that is, an ultrasound echo signal) reflected by an object in a 2D image, a Doppler spectrum image showing a velocity of a moving object in a Doppler spectrum by using a Doppler effect, a color Doppler image showing velocity and direction of a moving object in a color by using a Doppler effect, an elasticity image showing a reaction difference between a case of applying compression to an object and a case of not applying compression to the object, etc. Here, the color Doppler image shows a flow degree of blood flow in a corresponding color, and may be usefully used in verifying a disease of a blood vessel.

The controller 320 obtains blood flow information of an object by using a Doppler component obtained from ultrasound data. Here, the blood flow information may include at least one of the blood flow velocity, a blood flow amount, a blood flow pressure, and a blood flow angle. The controller 320 may set a plurality of sample volume gates based on the blood flow information.

The controller 320 may obtain the blood flow information by using vector information representing blood flow velocity and direction of an object. Specifically, the controller 320 may obtain the vector information by using a vector Doppler method. The vector Doppler method includes a cross beam-based method and a plane wave-based method, and is not limited thereto. The cross beam-based method obtains a vector having a 2D or 3D direction and magnitude information by obtaining velocity magnitude components from two or more other directions and combining the same. When the plane wave-based Doppler technology is used, the controller 320 may obtain blood flow information, and obtain, at a time, a plurality of points at which sample volume gates may be set. Therefore, the controller 320 may obtain a plurality of Doppler spectrums even without repeatedly obtaining an ultrasound image.

The controller 320 may estimate a stream line corresponding to blood flow by using vector information, and set a point having a maximum magnitude of a blood flow velocity on the stream line to a first sample volume gate. Also, the controller 320 may set a second sample volume gate according to a predetermined criterion based on the stream line and the first sample volume gate. Here, the predetermined criterion includes setting a point having a minimum magnitude of a blood flow velocity inside an interested region of an ultrasound image and/or a point at which a magnitude of a blood flow velocity is less than a predetermined criterion value to a second sample volume gate. The above-mentioned predetermined criterion may include a criterion within a range easily changeable by a person of ordinary skill in the art. For example, in the case of the carotid, the controller 320 may set a sample volume gate at a point separated by 1 cm from a common carotid artery (CCA) start point.

Specifically, in the case where an object is the carotid, the controller 320 may set a first sample volume gate at a predetermined location of a constriction portion in response to a location of a maximum constriction point from among the constriction portion of the carotid. Here, the first sample volume gate may be set at a location corresponding to a point having a fastest blood flow velocity. The controller 320 may set a second sample volume gate besides the first sample volume gate. The second sample volume gate may be located on a continuous line of blood flow at which the first sample volume gate is located, and set at a location where a change in a velocity on the continuous line is less than a predetermined criterion value.

Also, the controller 320 controls the display 330 to display a predetermined screen. The display 330 allows a user or a patient to visually recognize a predetermined image or information by displaying the predetermined image. The display may correspond to the display 330 illustrated in FIG. 1, and may be a separate component independent of the ultrasound diagnosis apparatus illustrated in FIG. 1.

The display 330 displays a predetermined screen. Specifically, the display 330 displays a predetermined screen under control of the controller 320. The display 330 may include a display panel (not shown), and display a user interface screen, a medical image screen, etc. on the display panel.

The display 330 displays an ultrasound image in which a plurality of sample gates are displayed. For example, the display 330 displays an ultrasound image in which a first sample volume gate and a second sample volume gate are displayed.

Also, the display 330 displays a plurality of Doppler spectrums respectively corresponding to a plurality of sample gates. Here, the plurality of Doppler spectrums have the same time information.

Figure 3B:
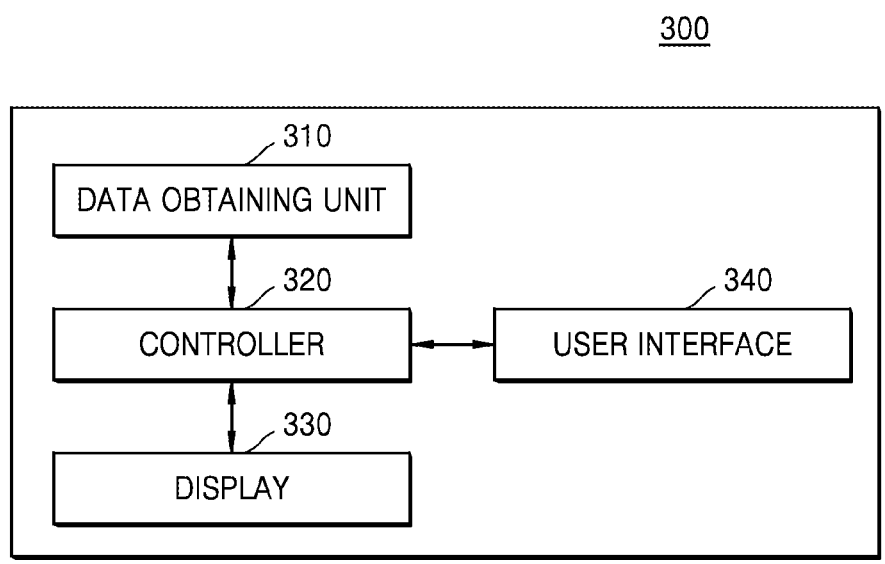
FIG. 3B is a block diagram illustrating a configuration of an ultrasound apparatus according to another exemplary embodiment.

FIG. 3B is a block diagram illustrating configuration of an ultrasound apparatus 300 according to another exemplary embodiment.

The ultrasound apparatus 300 illustrated in FIG. 3B may further include a user interface 340 compared with the ultrasound apparatus 300 illustrated in FIG. 3A.

Referring to FIG. 3B, since the data obtaining unit 310, the controller 320, and the display 330 of the ultrasound apparatus 300 equally correspond to the data obtaining unit 310, the controller 320, and the display 330 of the ultrasound apparatus 300, respectively, described with reference to FIG. 3A, repeated descriptions of FIG. 3A are omitted.

The user interface 340 denotes a device that receives data for controlling the ultrasound apparatus 300 from a user. The user interface 340 may include hardware configurations such as a keypad, a mouse, a touch panel, a touchscreen, a track ball, and a jog switch, but is not limited thereto. Also, the user interface 340 may further include various input units such as a voice recognition sensor, a gesture recognition sensor, a fingerprint recognition sensor, an iris recognition sensor, a depth sensor, and a distance sensor.

The user interface 340 receives a user input for setting at least one sample volume gate from among a plurality of sample volume gates at a predetermined location of an object displayed on an ultrasound image. The controller 320 sets at least one sample volume gate based on the user input.

The user interface 340 may generate and output a screen of the user interface 340 for receiving a predetermined command or data from a user. For example, the user interface 340 may generate and output a screen for setting at least one of an input for setting an interested region on an ultrasound image and an input for setting an interested location of at least one sample volume gate in the interested region.

Also, the user interface 340 may receive a predetermined command or data from a user via the screen of the user interface 340. For example, the user interface 340 may receive at least one of an input for moving an interested location to at least one scan line displayed on an ultrasound image, an input for setting a scan depth of at least one scan line in response to the interested location, and an input for setting an angle of a sample volume gate that corresponds to a stream line corresponding to blood flow of an object on a screen for setting the interested location. More specifically, the screen of the user interface 340 may receive a manipulation signal by a user's touch input via various input tools. The screen of the user interface 340 may receive a drag and drop signal of a scan line displayed on the screen and move the scan line by using a user's hand or a physical tool.

Obtaining a plurality of repeated ultrasound images may be avoided and an accurate diagnosis may be induced by adjusting so that a sample volume gate may be located on a correct location of an object via the user interface 340.

A user may visually recognize predetermined information by viewing the screen of the user interface 340 displayed via the display 330, and input a predetermined command or data via the user interface 340. For example, the user interface 340 may include a touchpad. Specifically, the user interface 340 may include a touchpad coupled with a display panel included in the display 330. In this case, the screen of the user interface 340 is output on the display panel. When a predetermined command is input via the screen of the user interface 340, the touchpad detects the predetermined command and transmits detected information to the controller 320. Then, the controller 320 may recognize and execute a predetermined command input by a user by analyzing the detected information.

The controller 320 may estimate a stream line corresponding to blood flow by using vector information representing velocity and direction of blood flow of an object. The controller 320 may set a point having a maximum magnitude of a blood flow velocity on the stream line to a first candidate sample volume gate. Also, the controller 320 may set a second candidate sample volume gate based on the stream line and the first candidate sample volume gate. Specifically, the controller 320 may set a point having a minimum magnitude of a blood flow velocity inside an interested region of an ultrasound image to the second candidate sample volume gate. A person of ordinary skill in the art will understand that a candidate sample volume gate may be set at a point having another clinical meaning (for example, in the case of the carotid, a point separated by 1 cm from a CCA start point) besides the point having the minimum magnitude of the blood flow velocity.

The display 330 may display an ultrasound image in which the first candidate sample volume gate and the second candidate sample volume gate are displayed. Here, the user interface 340 may receive a user input for adjusting at least one of the first candidate sample volume gate and the second candidate sample volume gate displayed on the display 330. Also, the user interface 340 may receive a user input that has determined at least one of the first candidate sample volume gate and the second candidate sample volume gate as a sample volume gate.

Also, the user interface 340 may receive an input of selecting the first sample volume gate from among the plurality of sample volume gates, and the display 330 may display a first Doppler spectrum corresponding to the first sample volume gate.

Also, the ultrasound apparatus 300 may further include a storage unit (not shown) and a communication module (not shown). The storage unit (not shown) may equally correspond to the memory 1500 of FIG. 1, and the communication module (not show) may equally correspond to the communication module 1300 of FIG. 1. The storage unit (not shown) may store data (for example, an ultrasound image, ultrasound data, scan-related data, a patient's diagnosis data, etc.) related to an ultrasound image, data transmitted from an external device to the ultrasound apparatus 300, etc. The data transmitted from the external device may include patient-related information, data required for diagnosis and treatment of a patient, a patient's previous treatment history, a medical work list corresponding to a diagnosis instruction for a patient, etc.

The communication module (not shown) may receive and/or transmit data from/to an external device. For example, the communication module may be connected with a wireless probe or an external device via a communication network that complies with WiFi or WiFi-direct. Specifically, a wireless communion network which the communication module may access includes a wireless local area network (LAN), a WiFi, Bluetooth, Zigbee, WiFi-direct (WFD), ultra wideband (UWB), infrared data association (IrDA), Bluethooth low energy (BLE), near field communication (NFC), etc., and is not limited thereto.

The ultrasound apparatus 300 may set a plurality of sample volume gates corresponding to an interested location of an object, and provide a Doppler spectrum for the plurality of sample volume gates by using an ultrasound image obtained one time.

The ultrasound apparatus 300 may generally control operations of the data obtaining unit 310, the controller 320, the display 330, and the user interface 340 by including a central operating processor. The central operating processor may include an array of a plurality of logic gates, and include a combination of a general-purpose microprocessor and a memory that stores a program executable by the microprocessor. Also, a person of ordinary skill in the art will understand that the central operating processor may include hardware of other forms.

Figure 3C:
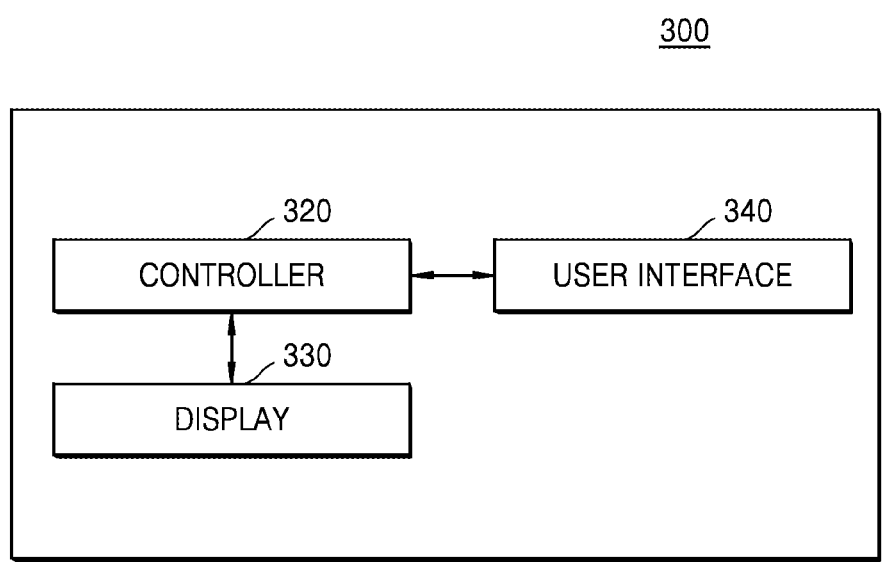
FIG. 3C is a block diagram illustrating a configuration of an ultrasound apparatus according to another exemplary embodiment.

FIG. 3C is a block diagram illustrating configuration of an ultrasound apparatus 300 according to still another exemplary embodiment.

According to an exemplary embodiment, the ultrasound apparatus 300 may include the controller 320, the display 330, and the user interface 340.

Since the controller 320, the display 330, and the user interface 340 illustrated in FIG. 3C may equally correspond to the controller 320, and the display 330 illustrated in FIG. 3A and the controller 320, the display 330, and the user interface 340 illustrated in FIG. 3B, repeated descriptions are omitted.

The user interface 340 receives a user input for setting at least one of a plurality of sample volume gates corresponding to an interested location of an object at a predetermined location of the object displayed on an ultrasound image.

The controller 320 sets at least one sample volume gate based on the user input.

The display 330 displays an ultrasound image obtained from ultrasound data. The display 330 displays the ultrasound image in which a plurality of sample volume gates are displayed.

Hereinafter, various operations or applications performed by the ultrasound apparatus 300 are described, and even when a certain component is not specified among the data obtaining unit 310, the controller 320, the display 330, and the user interface 340, content of a degree which a person of ordinary skill in the art may clearly understand and expect may be understood as general implementation, and the scope of the inventive concept is not limited by a name of a specific component or a physical/logical structure.

Figure 4:
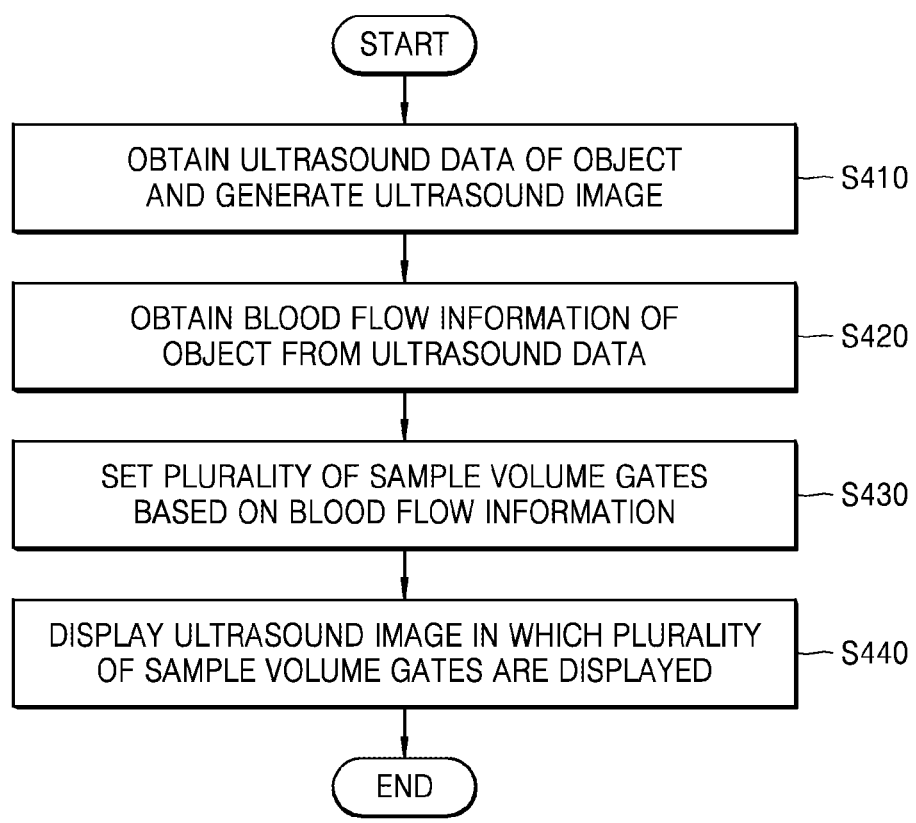
FIG. 4 is a flowchart illustrating a method of operating an ultrasound apparatus, according to an exemplary embodiment.

FIG. 4 is a flowchart illustrating a method of operating an ultrasound apparatus 300 according to an exemplary embodiment.

In operation S410 of FIG. 4, the ultrasound apparatus 300 obtains ultrasound data of an object. Here, the ultrasound data may be obtained from the ultrasound apparatus 300, and obtained by receiving the ultrasound data from an external device. The obtaining of the ultrasound data from the ultrasound apparatus 300 includes transmitting an ultrasound signal to an object and receiving an ultrasound signal reflected by the object. Here, the external device may be a storage unit. The storage unit includes all of a hard disk drive (HDD), read only memory (ROM), random access memory (RAM), flash memory, and a memory card.

In operation S420, the ultrasound apparatus 300 obtains blood flow information of an object from ultrasound data. Here, the blood flow information may include at least one of a blood flow velocity, a blood flow amount, a blood flow pressure, and a blood flow angle. The ultrasound apparatus 300 may obtain the blood flow information by using vector information representing blood flow velocity and direction of an object.

In operation S430, the ultrasound apparatus 300 sets a plurality of sample volume gates based on the blood flow information. The ultrasound apparatus 300 may set a point having a maximum blood flow velocity to a first sample volume gate by using the vector information, and set a point moved by a predetermined distance or angle from the first sample volume gate, to a second sample volume gate. As described above, when the ultrasound data is obtained, the ultrasound apparatus 300 may set a plurality of sample volume gates.

Also, the ultrasound apparatus 300 may set a plurality of candidate sample volume gates and configure and display, on a screen, an ultrasound image in which the plurality of candidate sample volume gates are displayed. The ultrasound apparatus 300 may set a plurality of sample volume gates by receiving an input of correcting at least one of the plurality of candidate sample volume gates, and an input of determining a sample volume gate. A process of setting a sample volume gate by using a candidate sample volume gates is described with reference to FIG. 5.

In operation S440, the ultrasound apparatus 300 displays an ultrasound image in which a plurality of sample volume gates are displayed. Also, the ultrasound apparatus 300 may display a plurality of Doppler spectrums that respectively correspond to the plurality of sample volume gates. Here, the plurality of Doppler spectrums have the same time information.

Also, the ultrasound apparatus 300 may receive a first sample volume gate from among the plurality of sample volume gates, and display a first Doppler spectrum corresponding to the first sample volume gate.

Figure 5:
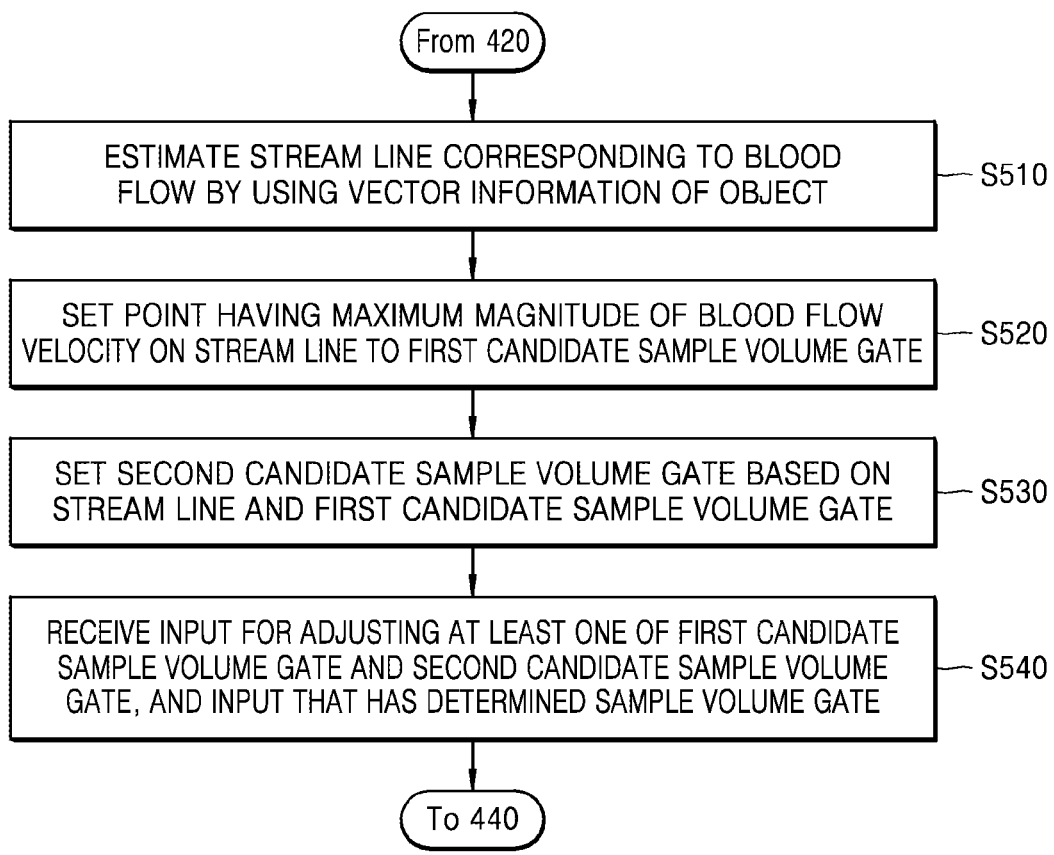
FIG. 5 is a flowchart illustrating a method of setting a sample volume gate, according to an exemplary embodiment.

FIG. 5 is a flowchart illustrating a method of setting a sample volume gate according to an exemplary embodiment.

In operation S510 of FIG. 5, the ultrasound apparatus 300 estimates a stream line corresponding to blood flow by using vector information of an object.

In operation S520, the ultrasound apparatus 300 sets a point having a maximum magnitude of a blood flow velocity on the stream line to a first candidate sample volume gate.

In operation S530, the ultrasound apparatus 300 sets a second candidate sample volume gate based on the stream line and the first candidate sample volume gate. The ultrasound apparatus 300 may set a point where a magnitude of a blood flow velocity is less than a predetermined criterion value to the second candidate sample volume gate. For another example, the ultrasound apparatus 300 may set a point having a minimum magnitude of a blood flow velocity inside an interested region of an ultrasound image to the second candidate sample volume gate. A person of ordinary skill in the art will understand that a candidate sample volume gate may be set at a point having another clinical meaning (for example, in the case of the carotid, a point separated by 1 cm from a CCA start point) besides the point having the minimum magnitude of the blood flow velocity.

In operation S540, the ultrasound apparatus 300 sets a plurality of sample volume gates by using a plurality of candidate sample volume gates. Specifically, the ultrasound apparatus 300 may receive an input of adjusting at least one of the first candidate sample volume gate and the second candidate sample volume gate. Also, the ultrasound apparatus 300 may receive a user input that has determined at least one of the first candidate sample volume gate and the second candidate sample volume gate as the plurality of sample volume gates.

Figure 6:
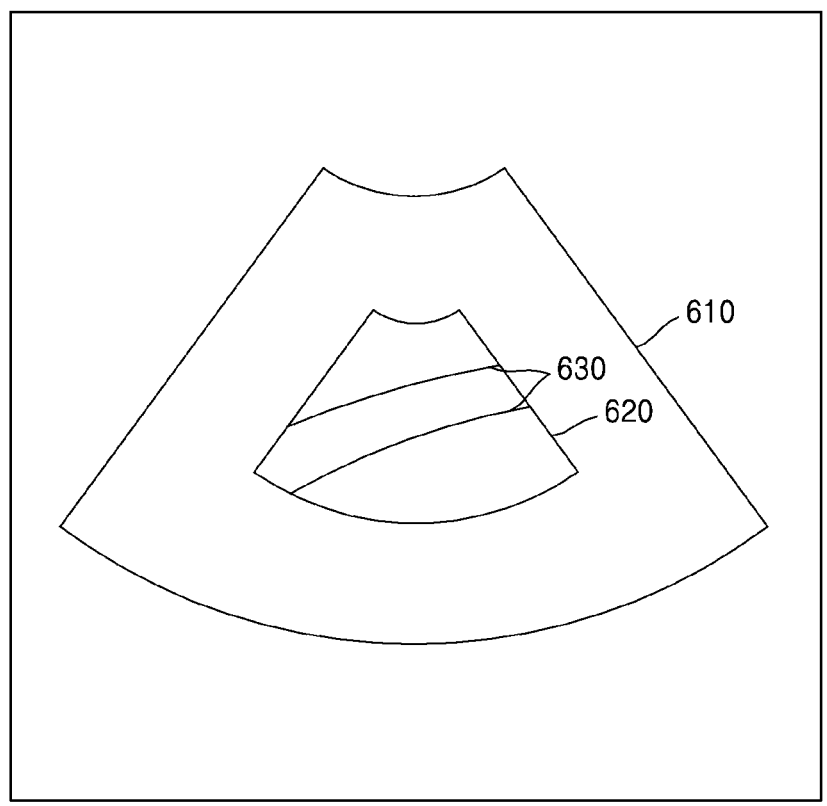
FIG. 6 is a diagram for explaining a screen that displays an ultrasound image in an ultrasound apparatus, according to an exemplary embodiment.

FIG. 6 is a diagram for explaining a screen that displays an ultrasound image in an ultrasound apparatus 300 according to an exemplary embodiment.

The ultrasound apparatus 300 generates an ultrasound image by using ultrasound data. As an example of a mode (referred to as a composite mode) that provides a plurality of ultrasound images, the ultrasound apparatus 300 includes a brightness (B)-mode for providing a B-mode image, a color (C)-Doppler mode or power (P)-Doppler mode for providing a color flow image, and a Doppler (D)-mode for providing a Doppler spectrum. Here, the color flow image includes a color Doppler image and a power Doppler image.

Referring to FIG. 6, the ultrasound apparatus 300 displays an ultrasound image, and receives a user input for setting an interested region ROI 620 at the ultrasound image. The interested region 620 includes a color box for obtaining a vector Doppler image by using vector information (that is, vector information corresponding to blood flow velocity and direction of an object) of the object. Also, 630 represents a blood vessel. The ultrasound apparatus 300 receives a user input for setting an interested location at which a plurality of sample volume gates are located from among the interested region 620. Here, the user input is input from a control panel, a track ball, a mouse, a keyboard, etc.

Figure 7:
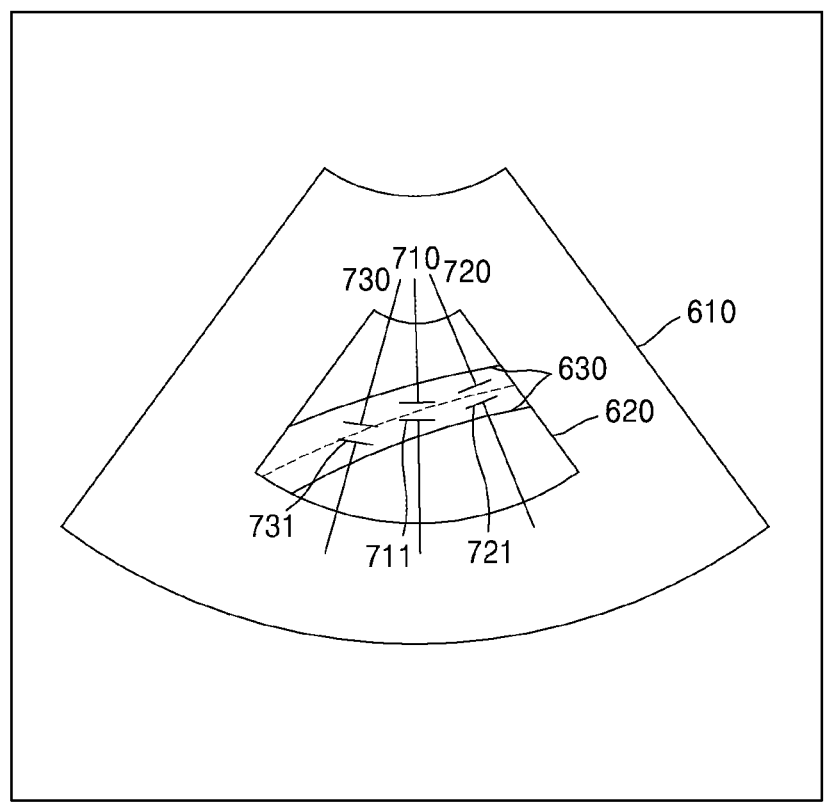
FIG. 7 is a diagram for explaining a screen that displays a sample volume gate at a predetermined location of an object displayed on an ultrasound image, according to an exemplary embodiment.

FIG. 7 is a diagram for explaining a screen that displays a sample volume gate at a predetermined location of an object displayed on an ultrasound image 610 according to an exemplary embodiment.

Referring to FIG. 7, the ultrasound apparatus 300 displays the ultrasound image 610 at which the interested region 620 is set. Also, the ultrasound apparatus 300 displays the ultrasound image 610 that displays a plurality of sample volume gates at a predetermined location of an object.

The ultrasound apparatus 300 may estimate a stream line corresponding to blood flow by using vector information representing blood flow velocity and direction of an object. 630 represents a blood vessel. The ultrasound apparatus 300 may set a point having a maximum magnitude of a blood flow velocity on the stream line to a first sample volume gate 711. The ultrasound apparatus 300 may display a first sample volume gate 711 and a first scan line 710 corresponding to the first sample volume gate 711 on a predetermined location of the object. Moving, at the ultrasound apparatus 300, the first scan line 710 based on a user input and resetting the first sample volume gate 711 are described with reference to FIGS. 8 and 9.

The ultrasound apparatus 300 may set points (for example, a point having a minimum magnitude of a blood flow velocity) having a clinical meaning in a plurality of interested regions to a second sample volume gate 721 and a third sample volume gate 731 based on the stream line and the first sample volume gate 711. As illustrated in FIG. 7, the ultrasound apparatus 300 may display a second scan line 720 and a third scan line 730 for resetting the second sample volume gate 721 and the third sample volume gate 731 on a screen. When the location of the first sample volume gate 711 is determined, the ultrasound apparatus 300 may set the second sample volume gate 721 and the third sample volume gate 731 according to a predetermined distance ratio.

The ultrasound apparatus 300 may adjust the location and angle of the first sample volume gate 711 to the third sample volume gate 731 based on a user input. Here, the ultrasound apparatus 300 may perform location movement and/or angle adjustment of the rest of sample volume gates simultaneously by performing location movement and/or angle adjustment of one of the first sample volume gate 711 to the third sample volume gate 731. Also, the ultrasound apparatus 300 may individually adjust a location and/or angle of each of the first sample volume gate 711 to the third sample volume gate 731.

Figure 8:
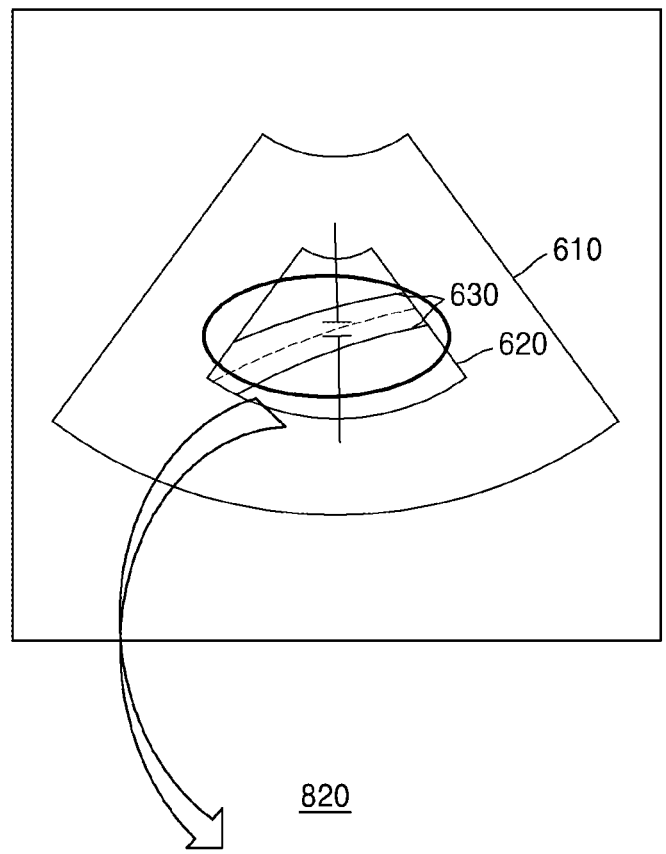
FIG. 8 is a diagram for explaining a screen that sets a sample volume gate at a predetermined location of an object displayed on an ultrasound image, according to an exemplary embodiment.
Figure 8:
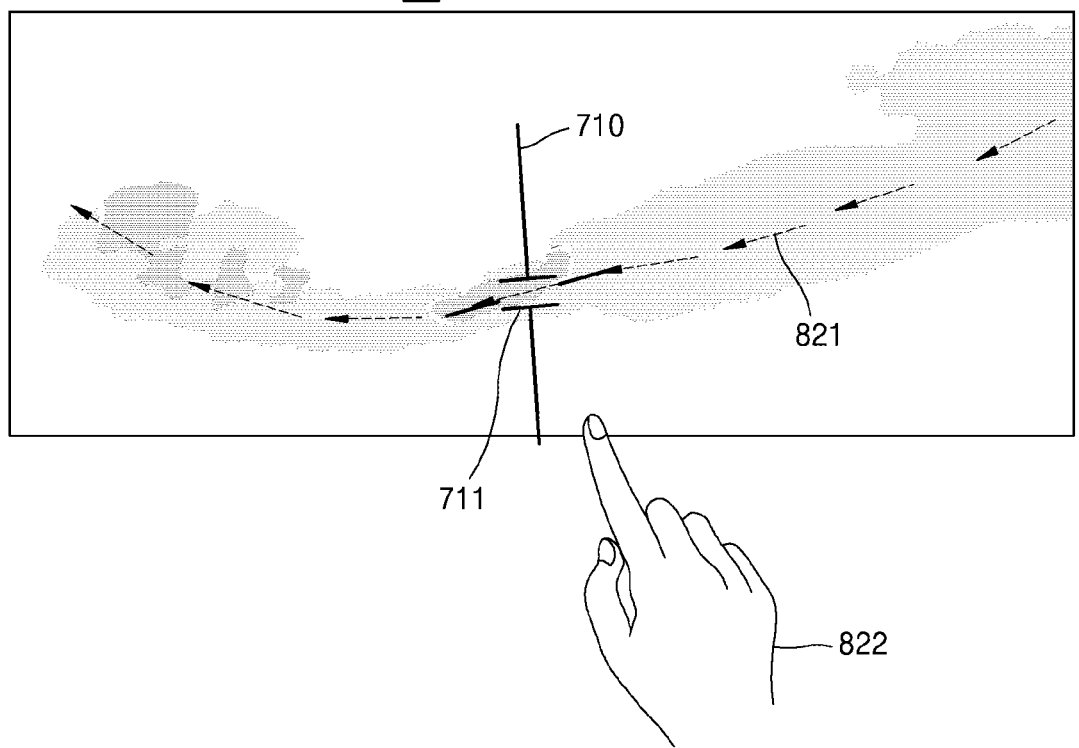

FIG. 8 is a diagram for explaining a screen that sets a sample volume gate at a predetermined location of an object displayed on an ultrasound image according to an exemplary embodiment.

Referring to 810 of FIG. 8, the ultrasound apparatus 300 displays an ultrasound image at which an interested region 620 is set. Here, an object may correspond to the carotid. 630 represents a blood vessel. The ultrasound apparatus 300 may set the first sample volume gate 711 serving as a criterion in order to set a plurality of sample volume gates 731, 732, and 733. Here, the setting of the sample volume gate may include setting the location and angle of the sample volume gate. The angle may be an angle formed by a stream line corresponding to blood flow of an object and a scan line.

A process of setting the first sample volume gate 711 may include extracting, at the ultrasound apparatus 300, a predetermined location of an object, and setting the first sample volume gate 711 in response to the predetermined location. The ultrasound apparatus 300 may use vector spectral Doppler technology in order to set the location and angle of the plurality of sample volume gates 731, 732, and 733.

Also, a process of setting another first sample volume gate 711 may include setting and displaying, at the ultrasound apparatus 300, a first candidate sample volume gate first, and setting the first sample volume gate 711 via a user's final input. The user may set the first sample volume gate 711 by adjusting the first scan line 710.

Referring to 820 of FIG. 8, the ultrasound apparatus 300 may receive a user input 822 for setting a sample volume gate. The ultrasound apparatus 300 may set a sample volume gate based on the user input 822. The ultrasound apparatus 300 may receive at least one of an input for moving an interested location of a sample volume gate to the first scan line 710 displayed on an ultrasound image 610, an input for setting a scan depth of the first scan line 710, and an input for setting an angle of a sample volume gate that corresponds to a stream line 821 corresponding to blood flow of an object.

Specifically, a user may move the interested location of the sample volume gate to the first scan line 710 by using a keypad, a mouse, a touch panel, a touchscreen, a track ball, a jog switch, etc. The user may adjust an angle formed by the stream line 821 corresponding blood flow of the object and the sample volume gate by adjusting a slope of the first scan line 710.

Figure 9:
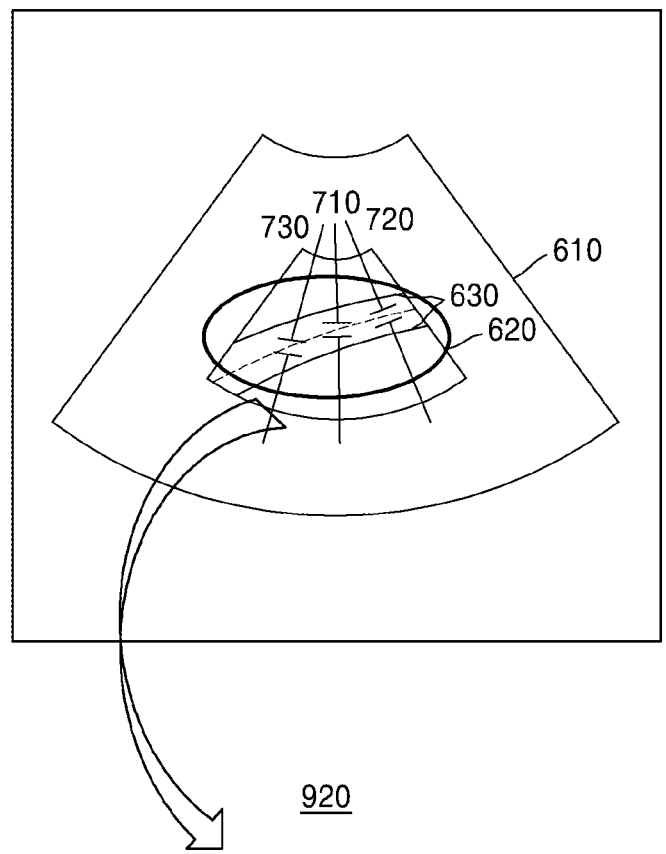
FIG. 9 is a diagram for explaining a screen that sets a sample volume gate at a predetermined location of an object displayed on an ultrasound image, according to another exemplary embodiment.
Figure 9:
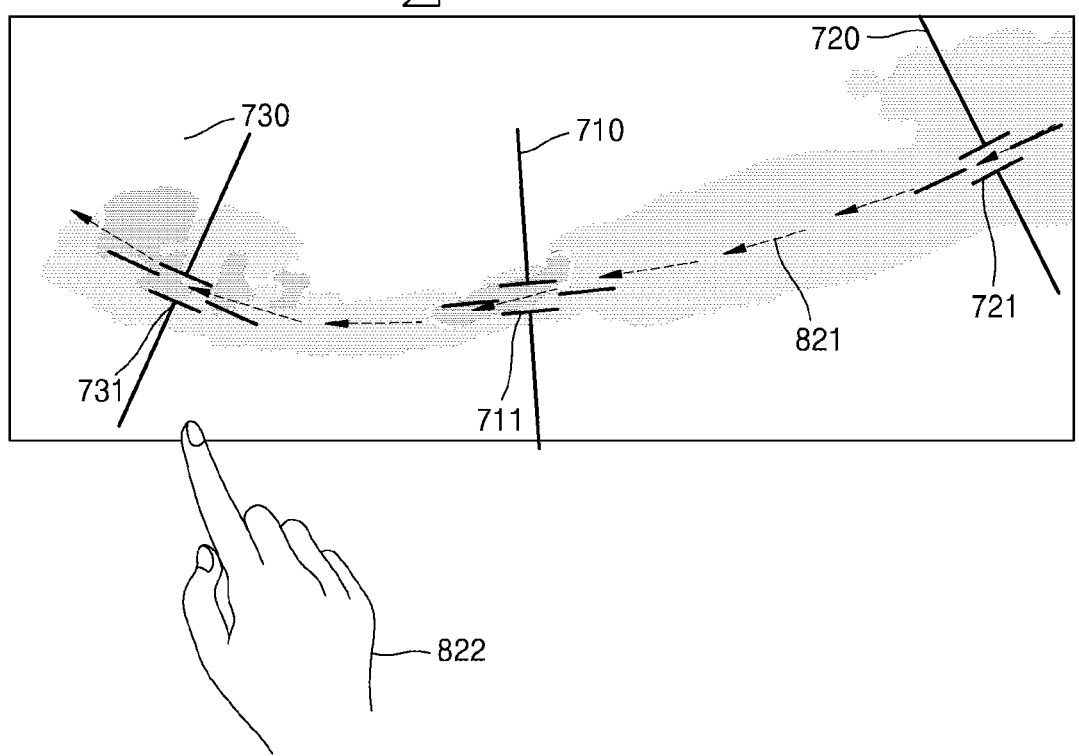

FIG. 9 is a diagram for explaining a screen that sets a sample volume gate at a predetermined location of an object displayed on an ultrasound image according to another exemplary embodiment.

Referring to 910 of FIG. 9, the ultrasound apparatus 300 displays an ultrasound image at which an interested region 620 is set. 630 represents a blood vessel. Also, the ultrasound apparatus 300 displays a plurality of sample volume gates 731, 732, and 733 on predetermined locations of an object displayed on the ultrasound image. The ultrasound apparatus 300 may extract a plurality of predetermined locations with respect to the object, and set the plurality of sample volume gates 731, 732, and 733 in response to the plurality of predetermined locations. Also, the ultrasound apparatus 300 may set and display a plurality of candidate sample volume gates, and set at least one of the plurality of candidate sample volume gates to a sample volume gate based on a user input.

Referring to 920 of FIG. 9, the ultrasound apparatus 300 may receive a user input 822 for setting the plurality of sample volume gates 731, 732, and 733. The ultrasound apparatus 300 may set the plurality of sample volume gates 731, 732, and 733 based on the user input 822. The ultrasound apparatus 300 may display a plurality of scan lines respectively corresponding to the plurality of sample volume gates 731, 732, and 733 on the ultrasound image 610. A user may adjust the location of a sample volume gate by moving a scan line.

The ultrasound apparatus 300 may set a point having a maximum magnitude of a blood flow velocity to a first sample volume gate 711. Also, the ultrasound apparatus 300 may set two points where a blood flow velocity is less than a predetermined criterion value to the second sample volume gate 721 and the third sample volume gate 731. The first sample volume gate 711 to the third sample volume gate 731 may be set on the stream line 821. When the user moves a first scan line 710, a second scan line 720 and a third scan line 730 may be changed simultaneously based on a direction and a distance in and by which the first scan line 710 is moved. Also, when a slope of the first scan line 710 is changed, slopes of the second scan line 720 and/or the third scan line 730 may be also changed simultaneously based on the change in the slope of the first scan line 710.

Figure 10:
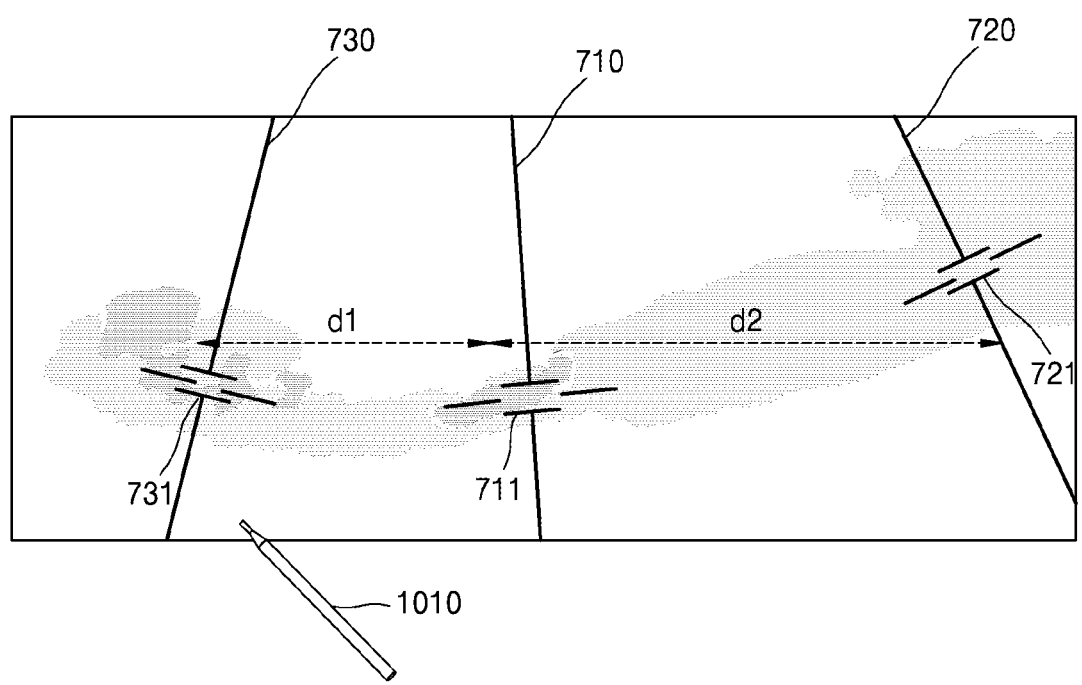
FIG. 10 is a diagram for explaining a screen that sets a sample volume gate, according to an exemplary embodiment.

FIG. 10 is a diagram for explaining a screen that sets a sample volume gate according to an exemplary embodiment.

The ultrasound apparatus 300 displays an ultrasound image in which the plurality of sample volume gates 731, 732, and 733 are displayed. The ultrasound apparatus 300 displays the plurality of scan lines 710, 720, and 730 used for setting a plurality of sample volume gates. The ultrasound apparatus 300 may receive an input for setting an interested location. The ultrasound apparatus 300 may receive an input for setting a predetermined location of an object to the interested location via a user interface. A user may parallel-move at least one of the plurality of scan lines 710, 720, and 730 by using the user interface. In this case, the user interface may receive a signal by using a touch input. The user interface may include a touch sensor or a proximity sensor in order to detect a user's touch input. For example, the touch sensor may have a form such as a touch film, a touch sheet, and a touchpad. The user interface may receive at least one manipulation signal from among the plurality of scan lines 710, 720, and 730 by a user's touch input via various input tools. Specifically, the user interface may receive at least one manipulation signal from among the plurality of scan lines 710, 720, and 730 by a user's hand, a physical tool 1010, a stylus pen, etc.

The ultrasound apparatus 300 may detect a touch input for moving at least one of the plurality of scan lines 710, 720, and 730, and display a screen that has moved the at least one of the plurality of scan lines 710, 720, and 730 from a first location to a second location of an object in response to the detected touch input.

Referring to FIG. 10, the ultrasound apparatus 300 displays a distance between the plurality of sample volume gates 731, 732, and 733 on an ultrasound image. Also, the ultrasound apparatus 300 may display an angle formed by a stream line corresponding to blood flow of an object and at least one of the scan lines 710, 720, and 730 on the ultrasound image.

Figure 11:
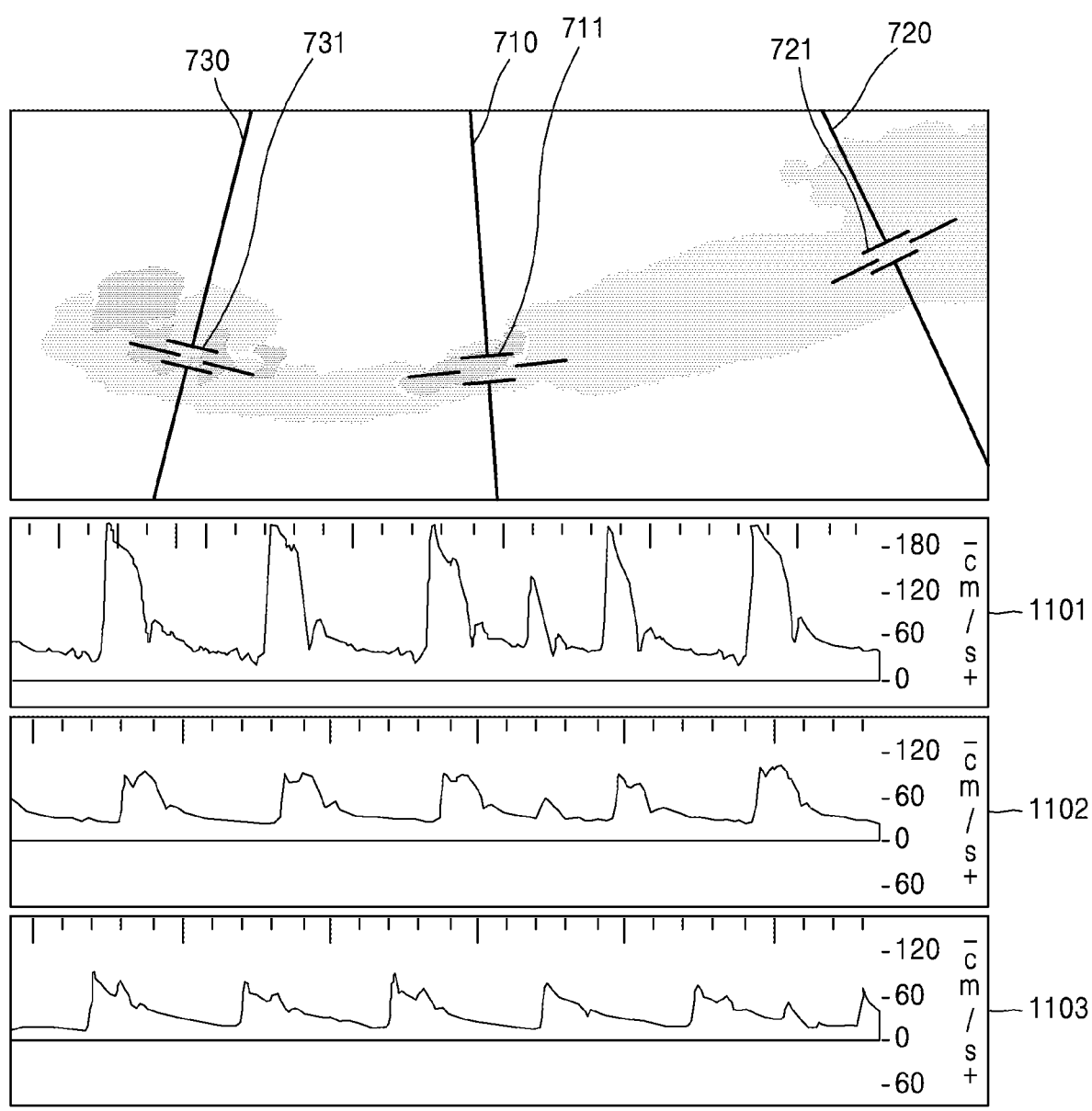
FIG. 11 is a diagram for explaining a screen provided by an ultrasound apparatus, according to an exemplary embodiment.

FIG. 11 is a diagram for explaining a screen provided by an ultrasound apparatus 300 according to an exemplary embodiment.

The ultrasound apparatus 300 generates an ultrasound image based on ultrasound data. The ultrasound apparatus 300 obtains blood flow information of an object by using a Doppler component obtained from the ultrasound data. The ultrasound apparatus 300 sets the plurality of sample volume gates 731, 732, and 733 at predetermined locations of the object based on the blood flow information. The ultrasound apparatus 300 displays the ultrasound image in which the plurality of sample volume gates 731, 732, and 733 are displayed. Referring to FIG. 11, the ultrasound apparatus 300 provides the ultrasound image that displays the first sample volume gate 711, the second sample volume gate 721, and the third sample volume gate 731 set at the predetermined locations of the object. A person of ordinary skill in the art will understand that the ultrasound apparatus 300 may set not only three sample volume gates but also a different number of sample volume gates.

The ultrasound apparatus 300 displays a plurality of Doppler spectrums 1101, 1102, and 1103 respectively corresponding to the plurality of sample volume gates 731, 732, and 733. Here, the plurality of Doppler spectrums 1101, 1102, and 1103 have the same time information.

The ultrasound apparatus 300 may receive a user input in order to set and/or edit at least one of the first sample volume gate 711, the second sample volume gate 721, and the third sample volume gate 731. The ultrasound apparatus 300 may set and/or reset at least one sample volume gate based on a user input. Here, the user input may include at least one of an input for moving the location of at least one sample volume gate displayed on an ultrasound image to at least one of the scan lines 710, 720, and 730, an input for setting a scan depth of the at least one of the scan lines 710, 720, and 730, and an input for setting an angle formed by a stream line corresponding to blood flow of an object and at least one of the sample volume gates 711, 721, and 731.

Referring to FIG. 11, the ultrasound apparatus 300 displays a Doppler spectrum corresponding to each of sample volume gates. Here, the ultrasound apparatus 300 may receive an input for selecting at least one sample volume gate from among the plurality of sample volume gates 731, 732, and 733, and display only a Doppler spectrum corresponding to the selected at least one sample volume gate.

Figure 12:
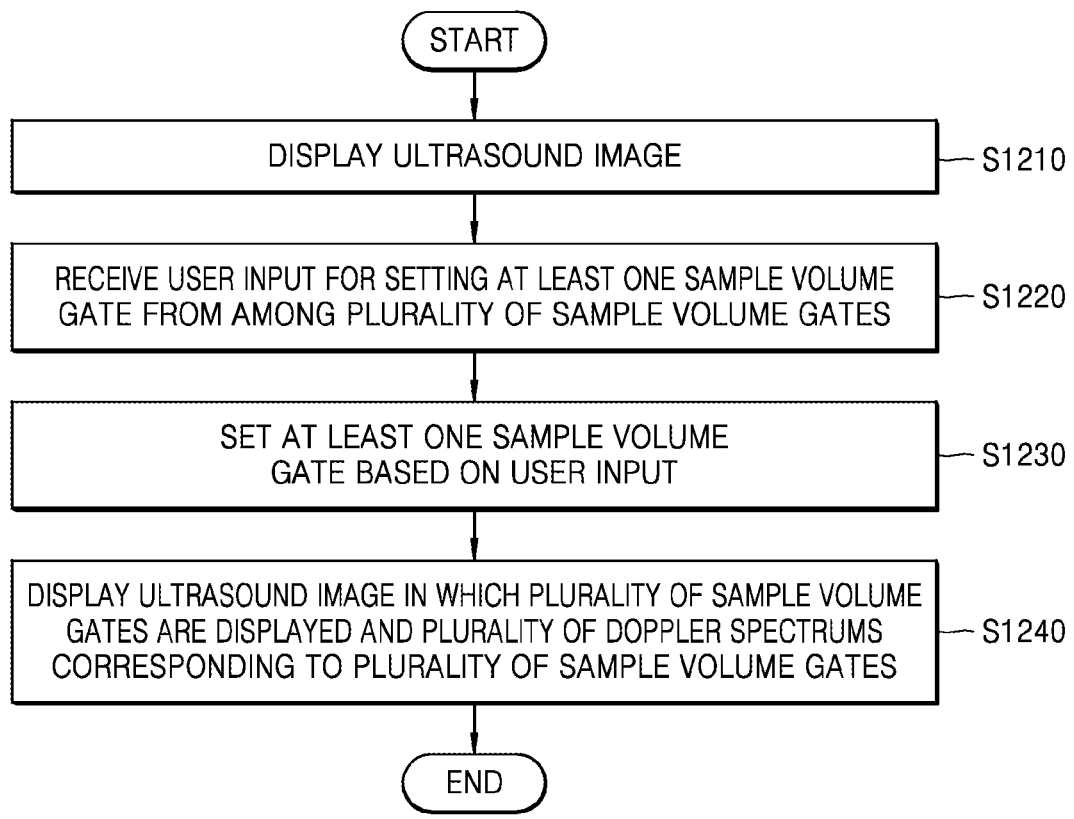
FIG. 12 is a flowchart illustrating a method of operating an ultrasound apparatus, according to another exemplary embodiment.

FIG. 12 is a flowchart illustrating a method of operating an ultrasound apparatus 300 according to another exemplary embodiment.

In operation S1210 of FIG. 12, the ultrasound apparatus 300 displays an ultrasound image. Here, the ultrasound image includes a brightness (B)-mode for providing a B-mode image, a color (C)-Doppler mode or power (P)-Doppler mode for providing a color flow image, and a Doppler (D)-mode for providing a Doppler spectrum.

In operation S1220, the ultrasound apparatus 300 receives a user's input for setting a sample volume gate. Specifically, the ultrasound apparatus 300 receives a user input for setting at least one of a plurality of sample volume gates corresponding to an interested location of an object at a predetermined location of the object displayed on the ultrasound image.

In operation S1230, the ultrasound apparatus 300 sets at least one sample volume gate based on a user input.

In operation S1240, the ultrasound apparatus 300 displays the ultrasound image in which a plurality of sample volume gates are displayed. Also, the ultrasound apparatus 300 may display a plurality of Doppler spectrums corresponding to the plurality of sample volume gates.

Figure 13A:
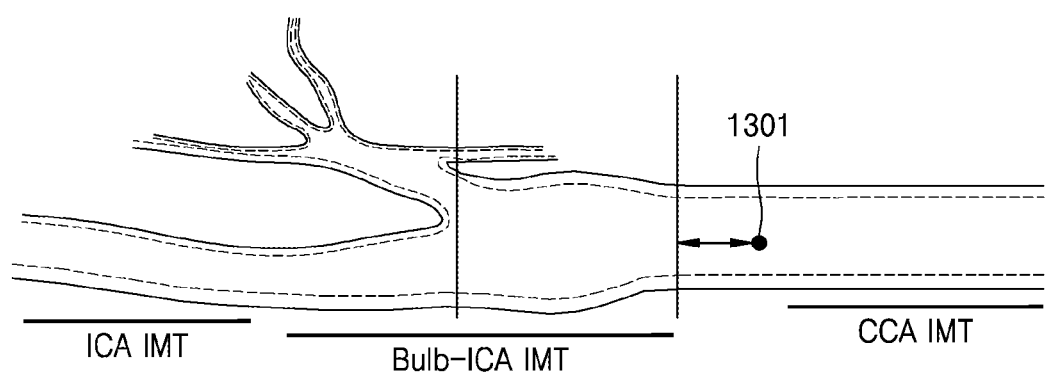
FIG. 13A is a diagram illustrating setting a sample volume gate in order to diagnose a carotid artery stenosis, according to an exemplary embodiment.

FIG. 13A is a diagram illustrating setting a sample volume gate in order to diagnose a carotid artery stenosis according to an exemplary embodiment.

According to an exemplary embodiment, in a Doppler mode of the ultrasound apparatus 300, the ultrasound apparatus 300 may set a sample volume gate at a maximum constriction point of internal carotid artery (ICA), and a point 1301 separated by a predetermined length (for example, 1 cm) from a start point of common carotid artery (CCA).

Figure 13B:
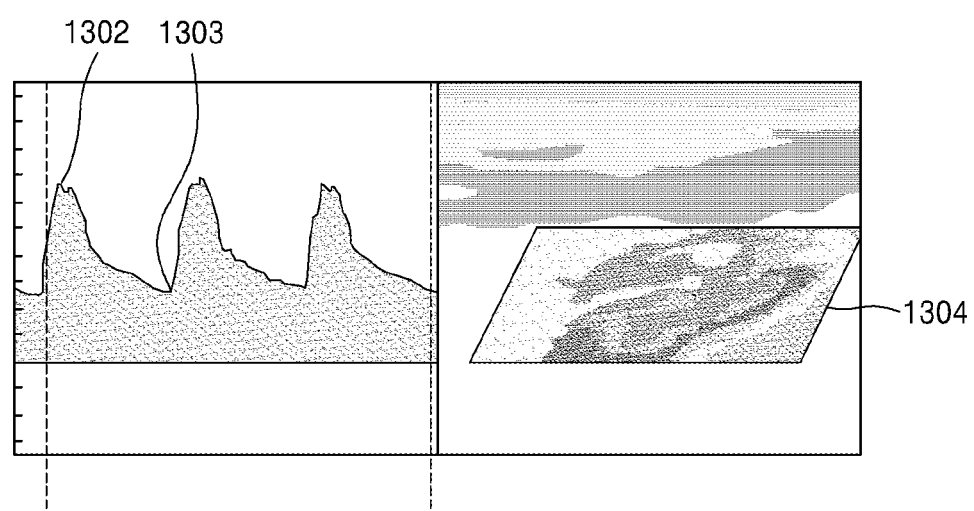
FIG. 13B is a diagram illustrating a screen that displays a graph related to a carotid artery stenosis, according to an exemplary embodiment.

FIG. 13B is a diagram illustrating a screen that displays a graph related to a carotid artery stenosis according to an exemplary embodiment.

Referring to FIG. 13B, a peak systolic velocity (PSV) value 1302 and an end diastolic velocity (EDV) value 1303 of a maximum constriction point of an ICA 1304 are illustrated.

Figure 13C:
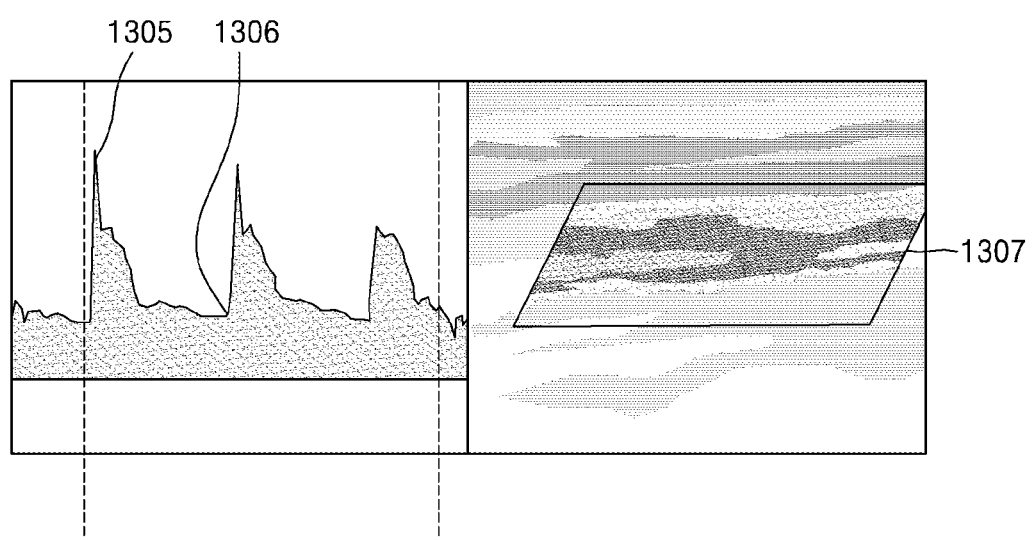
FIG. 13C is a diagram illustrating a screen that displays a graph related to a carotid artery stenosis, according to another exemplary embodiment.

FIG. 13C is a diagram illustrating a screen that displays a graph related to a carotid artery stenosis according to another exemplary embodiment.

Referring to FIG. 13C, a PSV value 1305 and an EDV value 1306 of a point separated by a predetermined length from a start point of a CCA 1307 are illustrated.

Figure 14:
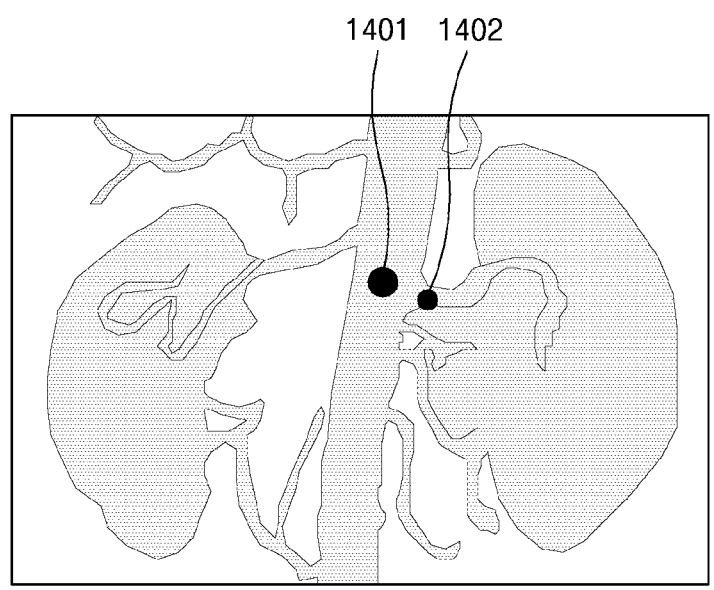
FIG. 14 is a diagram illustrating setting a sample volume gate in order to diagnose a renal artery stenosis, according to an exemplary embodiment.

FIG. 14 is a diagram illustrating setting a sample volume gate in order to diagnose a renal artery stenosis according to an exemplary embodiment.

The renal artery is an artery entering both kidneys from the aorta. The renal artery stenosis is a syndrome in which the renal artery narrows due to a certain cause. When a vessel constriction is observed by measuring the density of kidney at the renal artery and by a Doppler ultrasound and angiography, etc., renal artery stenosis may be diagnosed.

According to an exemplary embodiment, the ultrasound apparatus 300 may detect the abdominal aorta by scanning a longitudinal section right under at an end of the solar plexus. The ultrasound apparatus 300 may detect the renal artery extending to the left or right from the abdominal aorta. The ultrasound apparatus 300 may set a point 1401 of a peak systolic velocity of the aorta to a sample volume gate. Also, the ultrasound apparatus 300 may set a point 1402 of a peak systolic velocity at a renal maximum constriction point to a sample volume gate. When a ratio of a PSV of the kidney and a PSV of the aorta is 3.5 or more and/or a PSV of a maximum constriction point of the kidney is about 180-200 cm/s or more, a renal artery stenosis may be diagnosed.

Figure 15:
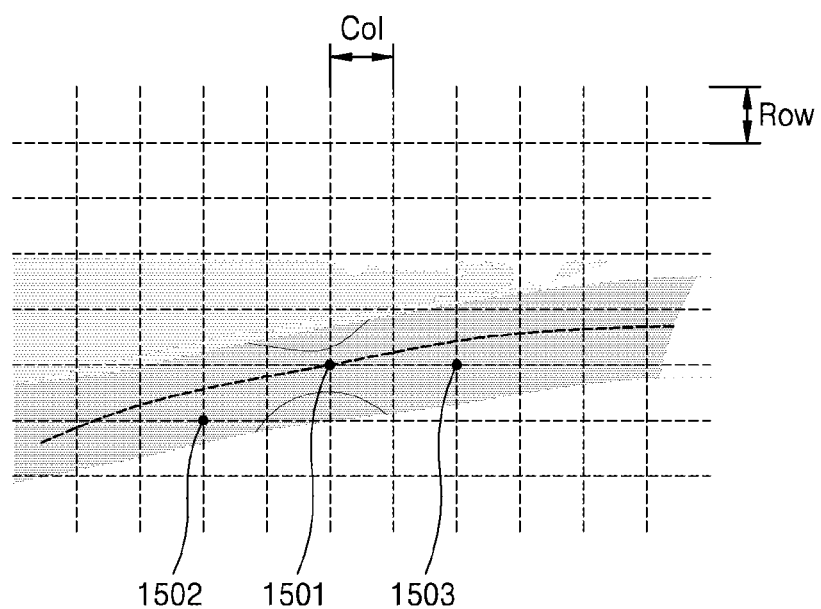
FIG. 15 is a diagram illustrating a screen that sets a candidate sample volume gate on an ultrasound image, according to an exemplary embodiment.

FIG. 15 is a diagram illustrating a screen that sets a candidate sample volume gate on an ultrasound image according to an exemplary embodiment.

The ultrasound apparatus 300 obtains ultrasound data of an object and generates an ultrasound image based on the ultrasound data. The ultrasound apparatus 300 displays the generated ultrasound image. The ultrasound apparatus 300 sets a plurality of sample volume gates by receiving a user input.

The ultrasound apparatus 300 may display lattice lines on the ultrasound image. The lattice lines may display column lines and row lines with a predetermined interval as illustrated in FIG. 15. The ultrasound apparatus 300 obtains blood flow information by using vector information representing blood flow velocity and direction of an object. The ultrasound apparatus 300 may estimate a stream line corresponding to blood flow by using the vector information, and set a point 1501 having a maximum magnitude of a blood flow velocity on the stream line to a first candidate sample volume gate. Here, the ultrasound apparatus 300 may move the lattice lines so that a first virtual lattice including a lattice line may coincide with a first candidate sample volume gate.

Also, the ultrasound apparatus 300 may set lattices 1502 and 1503 having a clinical meaning from among a plurality of virtual lattices to a second candidate sample volume gate and a third candidate sample volume gate. For example, the ultrasound apparatus 300 may set a point where the stream line meets a virtual lattice, a point having a fastest blood flow velocity, a point having a largest blood flow amount, a central point of a blood vessel, etc. to candidate sample volume gates. It is obvious to a person of ordinary skill in the art that the setting of the candidate sample volume gates at the ultrasound apparatus 300 is not limited to the above example and the sample volume gates may be set according to other criteria.

Figure 16:
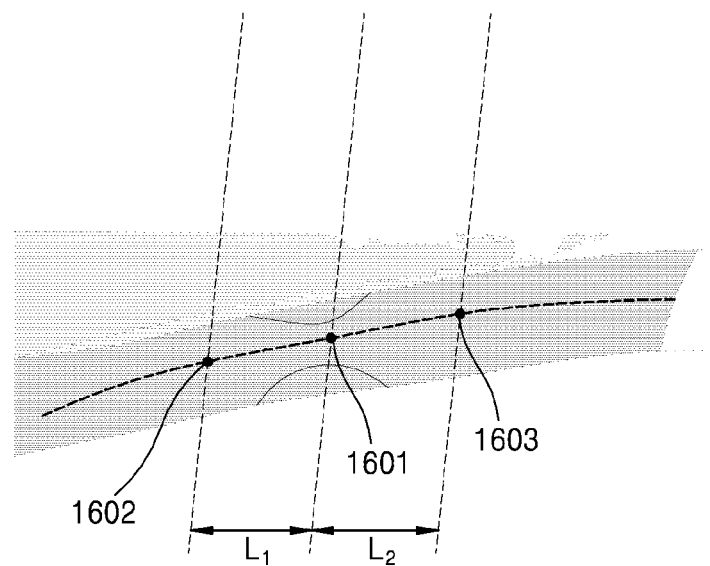
FIG. 16 is a diagram illustrating a screen that sets a candidate sample volume gate on an ultrasound image, according to another exemplary embodiment.

FIG. 16 is a diagram illustrating a screen that sets a candidate sample volume gate on an ultrasound image according to another exemplary embodiment.

The ultrasound apparatus 300 may estimate a stream line corresponding to blood flow by using vector information, and set a point 1601 having a maximum magnitude of a blood flow velocity on the stream line to a first candidate sample volume gate. The ultrasound apparatus 300 may set a point 1602 where a scan line of a point separated by L1 from the first candidate sample volume gate meets the stream line to a second candidate sample volume gate. Likewise, the ultrasound apparatus 300 may set a point 1603 where a scan line of a point separated by L2 from the first candidate sample volume gate meets the stream line to a third candidate sample volume gate. It is obvious to a person of ordinary skill in the art that L1 and L2 may be obtained from vector information representing blood flow velocity and direction of an object, and may be obtained from medical data, not the vector information.

Figure 17:
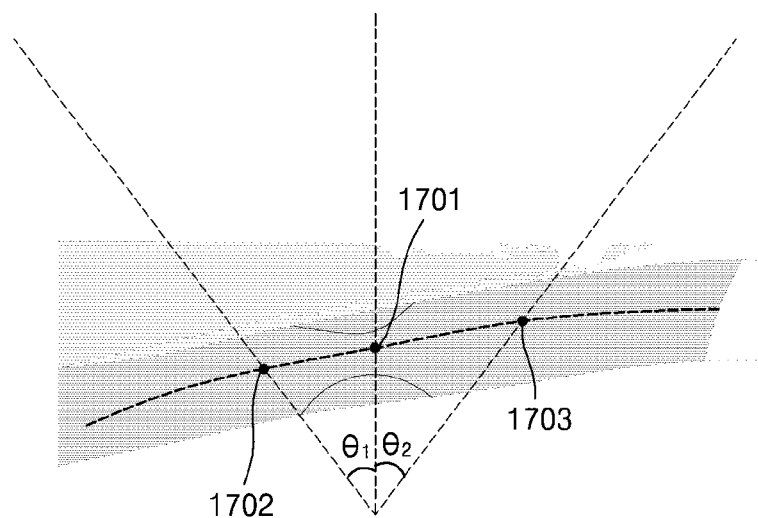
FIG. 17 is a diagram illustrating a screen that sets a candidate sample volume gate on an ultrasound image, according to another exemplary embodiment.

FIG. 17 is a diagram illustrating a screen that sets a candidate sample volume gate on an ultrasound image according to still another exemplary embodiment.

The ultrasound apparatus 300 may estimate a stream line corresponding to blood flow by using vector information, and set a point 1701 having a maximum magnitude of a blood flow velocity on the stream line to a first candidate sample volume gate. The ultrasound apparatus 300 may set a point 1702 where a scan line rotated by $\theta 1$ from a scan line in which the first candidate sample volume gate is located meets the stream line to a second candidate sample volume gate. Likewise, the ultrasound apparatus 300 may set a point 1703 where a scan line rotated by $\theta 2$ from the scan line in which the first candidate sample volume gate is located meets the stream line to a third candidate sample volume gate. It is obvious to a person of ordinary skill in the art that $\theta 1$ and $\theta 2$ may be obtained from vector information representing blood flow velocity and direction of an object, and may be obtained from medical data, not the vector information.

Figure 18:
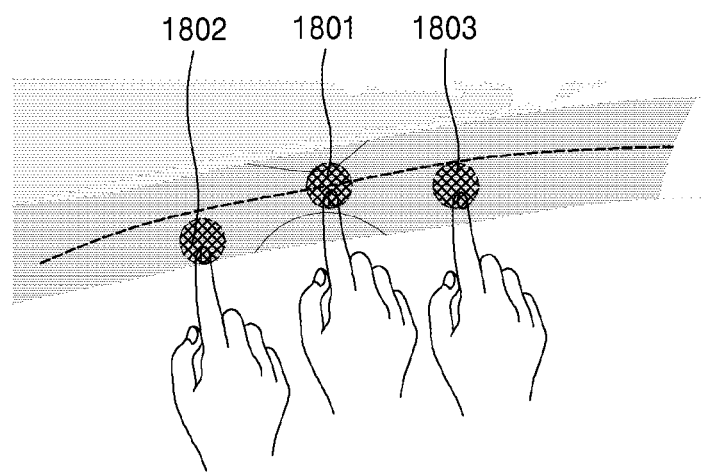
FIG. 18 is a diagram illustrating a screen that sets a candidate sample volume gate on an ultrasound image, according to another exemplary embodiment.

FIG. 18 is a diagram illustrating a screen that sets a candidate sample volume gate on an ultrasound image according to further another exemplary embodiment.

The ultrasound apparatus 300 may receive an input for setting an interested location of at least one candidate sample volume gate via a user interface. The user interface may receive a user input via a user's hand, a physical tool, a stylus pen, etc. Also, the user interface may be a touch panel that detects a touch input, and the touch panel may be configured integrally with a display of the ultrasound apparatus 300 and detect a touch input.

Referring to FIG. 18, the user may set a candidate sample volume gate on an ultrasound image displayed on the display of the ultrasound apparatus 300 by using a touch input. When the user inputs an approximate location of the candidate sample volume gate by using the touch, the ultrasound apparatus 300 may set a point having a maximum magnitude of a blood flow velocity inside a predetermined region around a first touch point 1801 to a first candidate sample volume gate. The predetermined region may have various shapes such as a circle, a quadrangle, etc. having the touch point as its center, and the size of the predetermined region may be set to a predetermined area.

Also, the ultrasound apparatus 300 may set a point having a maximum magnitude of a blood flow velocity inside a predetermined region around a second touch point 1802 to a second candidate sample volume gate. Likewise, the ultrasound apparatus 300 may set a point having a maximum magnitude of a blood flow velocity inside a predetermined region around a third touch point 1803 to a third candidate sample volume gate. Here, it is obvious to a person of ordinary skill in the art that a criterion for setting a candidate sample volume gate may be other criteria besides a point having a maximum magnitude of a blood flow velocity inside a predetermined region.

The above-described apparatus may be implemented by using a hardware component, a software component, and/or a combination of a hardware component and a software component. For example, the apparatus and the component described in the exemplary embodiments may be implemented by using one or more general-purpose computers or a special-purpose computers such as, for example, a processor, a controller, an arithmetic logic unit (ALU), a digital signal processor, a microcomputer, a field programmable array (FPA), a programmable logic unit (PLU), a microprocessor, or any device that may execute an instruction and respond thereto.

A processor may execute an operating system (OS) and one or more software applications executed on the OS. Also, the processor may access, store, manipulate, process, and generate data in response to execution of software.

For convenience of understanding, though description has been made to the case where one processor is used, a person of ordinary skill in the art will understand that the processor may include a plurality of processing elements and/or processing elements having a plurality of types. For example, the processor may include a plurality of processors, or one processor and one controller. Also, the processor may include a different processing configuration such as a parallel processor.

Software may include a computer program, a code, an instruction, or a combination of one or more of these, and configure the processor to operate as desired, or instruct the processor independently or collectively.

Software and/or data may be embodied permanently or temporarily in a certain type of a machine, a component, a physical device, virtual equipment, a computer storage medium or device, or a transmitted signal wave in order to allow the processor to analyze the software and/or data, or to provide an instruction or data to the processor. Software may be distributed on a computer system connected via a network, and stored and executed in a distributed fashion. Software and data may be stored in one or more non-transitory computer-readable recording media.

The methods according to exemplary embodiments may be embodied in the form of program commands executable through various computer means, which may be recorded on a non-transitory computer-readable recording medium. The non-transitory computer-readable recording medium may include program commands, data files, and data structures either alone or in combination. The program commands recorded on the non-transitory computer-readable recording medium may be those that are especially designed and configured for the inventive concept, or may be those that are known and available to computer programmers skilled in the art.

Examples of the non-transitory computer-readable recording medium include magnetic recording media such as hard disks, floppy disks, and magnetic tapes, optical recording media such as CD-ROMs and DVDs, magneto-optical recording media such as floptical disks, and hardware devices such as ROMs, RAMs, and flash memories that are especially configured to store and execute program commands.

Examples of the program commands include machine language codes that may be generated by a compiler, and high-level language codes that may be executed by a computer by using an interpreter.

The above hardware device may be configured to operate as one or more software modules in order to perform an operation of an exemplary embodiment, and vice versa.

Though the exemplary embodiments have been described by a limited number of exemplary embodiments and drawings, a person of ordinary skill in the art will make various modifications and changes from the above exemplary embodiments. For example, even when the described technologies are performed in an order different from the described method and/or components such as the described system, structure, apparatus, and circuit are coupled or combined in a form different from the described method, or replaced by other components or equivalents thereof, a proper result may be accomplished.

Therefore, the scope of the inventive concept should not be limited and determined by the described exemplary embodiments, but should be determined by not only the following claims but also equivalents thereof.

What is claimed is:

1. An ultrasound apparatus comprising:
a probe configured to obtain ultrasound data of an object;
a controller configured to generate an ultrasound image based on the ultrasound data, obtain blood flow information of the object by using a Doppler component obtained from the ultrasound data, set a plurality of sample volume gates based on the blood flow information, and obtain a plurality of Doppler spectrums for locations in which the plurality of sample volume gates are set; and
a display configured to display the ultrasound image in which the plurality of sample volume gates are displayed, and display a plurality of scan lines respectively corresponding to the plurality of sample volume gates on the ultrasound images; and
an input device configured to receive a first user input for moving a scan line of a first sample volume gate among from among the plurality of sample volume gates,
wherein the controller resets the first sample volume gate based on the first user input, and
wherein the display displays the reset first sample volume gate on the ultrasound image.

2. The apparatus of claim 1,
wherein the input device receives a user input for setting at least one sample volume gate from among the plurality of sample volume gates at a predetermined location of the object displayed in the ultrasound image, and
wherein the controller sets the at least one sample volume gate based on the user input.

3. The apparatus of claim 2, wherein the user input comprises at least one of an input for setting a region of interest in the ultrasound image and an input for setting an location of interest of the at least one sample volume gate in the region of interest.

4. The apparatus of claim 3, wherein the input for setting the location of interest comprises at least one of an input for moving the location of interest to at least one scan line displayed on the ultrasound image, an input for setting a scan depth of the at least one scan line in response to the location of interest, and an input for setting an angle of at least one sample volume gate that corresponds to a stream line corresponding to blood flow of the object.

5. The apparatus of claim 1, wherein the controller obtains the blood flow information by using vector information representing blood flow velocity and direction of the object.

6. The apparatus of claim 5, wherein the blood flow information comprises at least one of the blood flow velocity, a blood flow amount, a blood flow pressure, and a blood flow angle.

7. The apparatus of claim 5, wherein the controller estimates a stream line corresponding to the blood flow for setting the plurality of sample volume gates by using the vector information, and sets a first candidate sample volume gate indicating a candidate of the first sample volume gate at a point having a maximum magnitude of a blood flow velocity on the stream line.

8. The apparatus of claim 7, wherein the controller sets a second candidate sample volume gate based on the stream line and the first candidate sample volume gate.

9. The apparatus of claim 8, wherein the display displays the ultrasound image in which the first candidate sample volume gate and the second candidate sample volume gate are displayed.

10. The apparatus of claim 9, further comprising:
an input device configured to receive a user input that determines at least one of the first candidate sample volume gate and the second candidate sample volume gate as the at least one sample volume gate.

11. The apparatus of claim 10, wherein the input device receives a user input for adjusting at least one of the first candidate sample volume gate and the second candidate sample volume gate.

12. The apparatus of claim 1, wherein the object comprises a carotid artery or a renal artery.

13. The apparatus of claim 12, wherein the controller sets a first sample volume gate at a predetermined location of the carotid artery on the ultrasound image in response to a maximum constriction point from among a constriction portion of the carotid artery.

14. The apparatus of claim 1, wherein the display displays a plurality of Doppler spectrums respectively corresponding to the plurality of sample volume gates.

15. The apparatus of claim 14, wherein the plurality of Doppler spectrums are obtained at the same time.

16. The apparatus of claim 2, wherein the input device receives an input for selecting a first sample volume gate from among the plurality of sample volume gates, and the display displays a first Doppler spectrum corresponding to the first sample volume gate.

17. An ultrasound apparatus comprising:
a display configured to display an ultrasound image obtained from ultrasound data of an object, and display a plurality of sample volume gates and a plurality of scan lines respectively corresponding to the plurality of sample volume gates on the ultrasound image;
an input device configured to receive a user input for setting at least one of the plurality of sample volume gates corresponding to a location of interest of the object at a predetermined location of the object displayed in the ultrasound image; and
a controller configured to set the at least one sample volume gate based on the user input, and obtain a plurality of Doppler spectrums for locations in which the plurality of sample volume gates are set,
wherein the input device receives a first user input for moving a scan line of a first sample volume gate among from among the plurality of sample volume gates,
wherein the controller resets the first sample volume gate based on the first user input, and
wherein the display displays the reset first sample volume gate on the ultrasound image.

18. A method of operating an ultrasound apparatus, the method comprising:
obtaining ultrasound data of an object, and generating an ultrasound image based on the ultrasound data;
obtaining blood flow information of the object by using a Doppler component obtained from the ultrasound data;
setting a plurality of sample volume gates based on the blood flow information;
obtaining a plurality of Doppler spectrums for locations in which the plurality of sample volume gates are set;
displaying the ultrasound image in which the plurality of sample volume gates are displayed, and a plurality of scan lines respectively corresponding to the plurality of sample volume gates on the ultrasound image;
receiving a first user input for moving a scan line of a first sample volume gate among from among the plurality of sample volume gates;
resetting the first sample volume gate based on the first user input; and
displaying the reset first sample volume gate on the ultrasound image.

19. The method of claim 18, further comprising:
receiving a user input for setting at least one sample volume gate from among the plurality of sample volume gates at a predetermined location of the object displayed in the ultrasound image,
wherein the setting of the plurality of sample volume gates comprises:
setting the at least one sample volume gate based on the user input.

20. The method of claim 19, wherein the receiving of the user input comprises:
receiving at least one of an input for setting a region of interest in the ultrasound image and an input for setting a location of interest of the at least one sample volume gate in the region of interest.

21. The method of claim 20, wherein the receiving of the user input comprises:
receiving at least one of an input for moving the location of interest to at least one scan line displayed on the ultrasound image, an input for setting a scan depth of the at least one scan line in response to the location of interest, and an input for setting an angle of at least one sample volume gate that corresponds to a stream line corresponding to blood flow of the object.

22. The method of claim 18, wherein the obtaining of the blood flow information of the object comprises:
obtaining the blood flow information by using vector information representing blood flow velocity and direction of the object.

23. The method of claim 22, wherein the setting of the plurality of sample volume gates comprises:
estimating a stream line corresponding to the blood flow for setting the plurality of sample volume gates by using the vector information, and setting a first candidate sample volume fate at a point having a maximum magnitude of a blood flow velocity on the stream line.

24. The method of claim 23, wherein the setting of the plurality of sample volume gates comprises:

setting a second candidate sample volume gate based on the stream line and the first candidate sample volume gate.

25. The method of claim 24, further comprising:
displaying the ultrasound image in which the first candidate sample volume gate and the second candidate sample volume gate are displayed.

26. The method of claim 25, further comprising:
receiving a user input that determines at least one of the first candidate sample volume gate and the second candidate sample volume gate as at least one sample volume gate of the plurality of sample volume gates.

27. The method of claim 26, further comprising:
receiving a user input for adjusting at least one of the first candidate sample volume gate and the second candidate sample volume gate.

28. A method of operating an ultrasound apparatus, the method comprising:
displaying an ultrasound image obtained from ultrasound data of an object;
displaying a plurality of sample volume gates and a plurality of scan lines respectively corresponding to the plurality of sample volume gates on the ultrasound image;
receiving a user input for setting at least one of the plurality of sample volume gates corresponding to a location of interest of the object at a predetermined location of the object displayed in the ultrasound image;
setting the at least one sample volume gate based on the user input; and
obtaining a plurality of Doppler spectrums for locations in which the plurality of sample volume gates are set,
wherein the receiving the user input comprises receiving a first user input for moving a scan line of a first sample volume gate among from among the plurality of sample volume gates, and
wherein the setting the at least one sample volume gate comprises resetting the first sample volume gate based on the first user input, and displaying the reset first sample volume gate on the ultrasound image.

* * * * *